US010351628B2

(12) United States Patent
Vigna et al.

(10) Patent No.: US 10,351,628 B2
(45) Date of Patent: Jul. 16, 2019

(54) ANTIBODY FRAGMENTS, COMPOSITIONS AND USES THEREOF

(71) Applicant: METIS PRECISION MEDICINE SB S.R.L., Turin (IT)

(72) Inventors: Elisa Vigna, Villarbasse (IT); Paolo Michieli, Rivalta di Torino (IT); Paolo Maria Comoglio, Turin (IT)

(73) Assignee: METIS PRECISION MEDICINE SB S.R.L., Turin (IT)

( * ) Notice: Subject to any disclaimer, the term of this patent is extended or adjusted under 35 U.S.C. 154(b) by 0 days.

(21) Appl. No.: 15/952,513

(22) Filed: Apr. 13, 2018

(65) Prior Publication Data

US 2018/0237527 A1 Aug. 23, 2018

Related U.S. Application Data

(62) Division of application No. 14/758,079, filed as application No. PCT/IB2014/058098 on Jan. 7, 2014, now Pat. No. 9,975,952.

(30) Foreign Application Priority Data

Jan. 9, 2013 (IT) .............................. TO2013A0012

(51) Int. Cl.

| | | |
|---|---|---|
| *A61K 39/00* | (2006.01) | |
| *A61K 45/06* | (2006.01) | |
| *C07K 16/28* | (2006.01) | |
| *A61K 39/395* | (2006.01) | |
| *A61K 48/00* | (2006.01) | |

(52) U.S. Cl.
CPC ...... *C07K 16/2863* (2013.01); *A61K 39/3955* (2013.01); *A61K 45/06* (2013.01); *A61K 48/0016* (2013.01); *A61K 2039/505* (2013.01); *C07K 2317/522* (2013.01); *C07K 2317/55* (2013.01); *C07K 2317/565* (2013.01); *C07K 2317/60* (2013.01); *C07K 2317/66* (2013.01); *C07K 2317/73* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | | |
|---|---|---|---|---|
| 5,686,292 A | * | 11/1997 | Schwall | ............. C07K 16/2863 424/133.1 |
| 7,892,550 B2 | * | 2/2011 | Dennis | ................. C07K 16/005 424/143.1 |
| 8,101,727 B2 | * | 1/2012 | Stover | ................. C07K 16/2863 424/130.1 |
| 8,388,958 B2 | | 3/2013 | Comoglio et al. | |
| 8,729,043 B2 | | 5/2014 | Comoglio et al. | |
| 2013/0058937 A1 | | 3/2013 | Auer et al. | |

FOREIGN PATENT DOCUMENTS

| | | |
|---|---|---|
| EP | 1718677 | 11/2006 |
| JP | 2010535032 A | 11/2010 |
| WO | 2007/090807 | 8/2007 |
| WO | 2009018386 A1 | 2/2009 |
| WO | 2010/145792 A8 | 12/2010 |
| WO | 2012/083370 | 6/2012 |
| WO | 2013026831 A1 | 2/2013 |

OTHER PUBLICATIONS

Constantinou, A., et al., Modulating the Pharmacokinetics of Therapeutic . . . , Biotechnology Letters, vol. 32, No. 5, pp. 609-622, 2010.
Weir, A. N. C., et al., Formatting Antibody Fragments to Mediate Specific . . . , Biochemical Society Transactions, vol. 30, No. 4, pp. 513-517, 2002.
Jazayeri J. A., et al., FC-Based Cytokines: Prospects for Engineering . . . , vol. 22, No. 1, pp. 11-26, 2008.
Ward, E. S., et al., The Effector Functions of Immunoglobulins: Implications . . . , Therapeutic Immunology, vol. 2, No. 2, pp. 77-94, 1995.
Knauf M. J., et al., Relationship of Effective Molecular Size to Systemic . . . , Journal of Biological Chemistry, vol. 263, No. 29, pp. 15064-15070, 1988.
Giovanni Pacchiana, et al., Monovalency Unleashes the Full Therapeutic . . . , Journal of Biological Chemistry, vol. 285, No. 46, pp. 36149-36157, 2010.
Prat M., et al., Agonistic Monoclonal Antibodies Agaist the MET Receptor . . . , University Press, vol. 111, No. part 2, pp. 237-247, 2012.
International Search Report issued in PCT Application No. PCT/IB2014/058098.
European Office Action based on Application No. 14701430.2 dated Jan. 26, 2017 (4 pages).
Office Action for corresponding Japanese Patent Application No. 2015-551243 (dated Oct. 31, 2017)(7 Pages).
Liu, et al., mAbs, 4(1): 17-23, Jan./Feb. 2012.

\* cited by examiner

*Primary Examiner* — Marianne P Allen
(74) *Attorney, Agent, or Firm* — Lucas & Mercanti, LLP

(57) ABSTRACT

An isolated nucleic acid encoding a monovalent antibody fragment comprising a first polypeptide comprising a light chain variable domain and two constant domains and a second polypeptide comprising a heavy chain variable domain and two constant domains, wherein two chain constant domains are light chain constant domains and two constant domains are CH1 heavy chain constant domains.

16 Claims, 18 Drawing Sheets
Specification includes a Sequence Listing.

Nucleotide sequence (SEQ ID No.:9)

5'-
atggagacagacacaatcctgctatggtgctgctctggttccagtcctcactgtgctgaccaatccagctcttgg
ctgtgtctcaggccagggcaccatcctgatcagccaaagtccagctccagctccagtagtagctacatctggtcaacaga
gaccaggacagccacccaaactcctcatcctgtcatcaaccttgatcgcatcgcagttagtgcagtgcagtggctggac
agcttcacctcaatcatcctgtggagaggagaatgtgcaaccctattctgtcaatctgtcttcatctccgccatctgatgagcagttgaaatggaactgcct
ctgttgtgcctgtgaataactctatcccagagacaggtcaccatcaagtgagcctgagcgctgagcagcagagagaaac
agagtgcacaagtcacgctgcgaactctgatgagcagtgaaatgaactgcagaagagaataacttcatccagagagg
accatctgctctcatctccgccatctgatgagcagtgaaatgaactggacttctgcctgcagacagcagaggacagcac
ccaaagtcaagtcaagtggataacctgagcgctgagccctcgagcaaagaaaacaaagtctgcctgaagtcacccatccagggcct
ctacagcctcagcagcagaccctgagcgctgagcaaagagagctcaacaggggagagtgttaa-3'

Figure 13B

Amino acid sequence (SEQ ID No.:10)

N term-
METDTILLWVLLLWVPGSTGDIVLTQSPASLAVSLGQRATISCKASQSVDYDGGSYMSWFQQRPG
QPPKLLISAASNLESGIPARFSGSGSGTDFTLNIHPVEEEDVATYYCQQSYEDPLTFGAGTKVEIKR
TVAAPSVFIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGECTVAAPSVFIFPPSDEQLKSGTASV
VCLLNNFYPREAKVQWKVDNALQSGNSQESVTEQDSKDSTYSLSSTLTLSKADYEKHKVYACEV
THQGLSSPVTKSFNRGEC- C term

Figure 14A

VH-CH1-CH1-TAGs

Nucleotide sequence (SEQ ID No.:1)

5'-
atggatggagctatatcatcctctttttgtagcaacagtacagatggccactcccagtcaactgcaacagcctggactgaactgt
gaagctggggcttcagtgaagctgtcctgcaagtctggctacaccttcactagctacgtaatccactgggtgaagcagaggcctga
caaggcctgagtgattggagagattaatccaagtagtggtcgtactaactacaatgagaaattcaagaacaaggtcacagtgactgta
gacaaatcttccacagcactacatgcaactcagcaacctgactgaggactctgcggtctattactgtgcaatagggcactggg
ccaaggcaccactctcacagtctctccagtcctggctcctgtctcaggcaaggctagcacttcccgacacggtctttcccctggcacc
acacctccggtgctgtccagtccctacagaccctaggagcaactccctcagaggtgtcgaagtgtccagcgtggtgtgacc
atgcaagtgaatcacaagccagcaacaagccaccgctggggacacagacggccaatcgtgcaagactactctccgaacgtga
gtctcccctgcaactggcgcctgacagcggtgccaagtgtgggcagactcgatgtctagcagtacctcccagaggg
cagtgtcgtgaactgacagccgtccccagcagctgcgcaccagcagctttggcaccaaggccaatgaatcacaagccagcaaggacaagaa
gttgagcccaaatctgtgacaaaactcacacaGGTGCCGCACCCCAGTTCGAAAAGGGCC
GCATGGAGCACCACCACCATGGCGCCGCATCACCATCACCACCATTAG-3'

Figure 14B

Amino acid sequence (SEQ ID No.:2)

N term-
MGWSYIILFLVATATDGHSQVQLQQPGTELVKPGASVKLSCKASGYTFTSYVIHWVKQRPGQGLE
WIGEINPSSGRTNYNEKFKNKVTVTVDKSSTAYMQLSNLTSEDSAVYYCASRGYWGQGTTLVSS
ASTKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCASTKGPSVFPLAPSSKSTSGGTAALGCLV
KDYFPEPVTVSWNSGALTSGVHTFPAVLQSSGLYSLSSVVTVPSSSLGTQTYICNVNHKPSNTKVD
KKVEPKSCDKTHTGAAWSHPQFEKGAAWSHPQFEKGAAHHHHHH-C term VL-CL-CH1-TAGs Figure 15A
Nucleotide sequence (SEQ ID No.:17)

5'-
atggagacagacaatctgctatggtgctgctgtcgctggttccagtcactgcactgtgaccaatccagctcttggct
gtgtctaggagagggccacatcctgcaagtgccagcacttgatactgtaatgatggtaggtatggtgttcaacagaga
ccaggacagcaccaaactcctcatctgtctgacatcaaccttgaatctggcatcccagccaggttagtgggactgctggacaga
cttcacctcaatatccatcctgtgagagaggagatgtgcaacatctatctgcaacaagttatcaagacccctcagttcggtgctgt
accaaggtggagatcaaaagaactggctgcaccatctgtcttccgccatcgatgagcagttgaaactgaactgcctcgtgt
gtgcctgtgataacttctatcccagagaggccaagtacagtggaaggtgataaccgctccaatcggtaactccaggagagtgc
acagagacaggcaaggacaccacaagctgagctgcaccctccaagcggtcacaaagagagttcaacaggagagtgcacagagggcacaatc
ggtcttccccctgcacctcctccaagagacaccctggggcacacagcggcgtgccaagactacttccagaccgtg
acggtgtgtgaactcaggcgcctcagcagttggcaccagacaactactgcaatcgaactacaggagccaaccaaggtggcaagaa
gtgagccgtcctccagcaggttgacaaaatctgagacaaaacatcacaGGTGCCGCATGGAGCACCCCCAGTTCGAAAAGGGGCC
GCATGGAGCACCCCCCAGTTCGAAAAGGGCCGCCGAGCACCCCCAGTTCGAAAAGG
GGCCGCACCACCATCACCATTAG-3'

Figure 15B
Amino acid sequence (SEQ ID No.:18)

N term-
METDTILLWVLLWVPGSTGDIVLTQSPASLAVSLGQRATISCKASQSVDYDGGSYMSWFQQRPGQ
PPKLLISAASNLESGIPARFSGSGSGTDFTLNIHPVEEEDVATYYCQQSYEDPLTFGAGTKVEIKRTV
AAPSVFIFPPSDEQLKSGTASVVCLLNNFYPREAKVQWKVDNALQSGNSQESVTEQDSKDSTYSL
SSTLTLSKADYEKHKVYACEVTHQGLSSPVTKSFNRGECASTKGPSVFPLAPSSKSTSGGTAALGC
LVKDYFPEPVTVSWNSGALTSGVHTFPAVLQSSGLYSLSSVVTVPSSSLGTQTYICNVNHKPSNTKV
DKKVEPKSCDKTHTGAAWSHPQFEKGAAWSHPQFEKGAAWSHPQFEKGAAHHHHHH-C term

Nucleotide sequence (SEQ ID No.:15)

5'-
atggatggagctatatcatctctttttgtagcaacagctacagatggccactcccagtcaactgcaactgcaacagcctgaactg
tgaagcctggcttcagtgaagtcctgcaagtctggagctacacctccacagttactgatacactggtgaagcaggctcctgg
acaaggccttgagtggattgagtggattgagaataatccactacagcggtcagtaaatcaagagaaatcaagaacaagtcacagtgactg
tagacaaatcttccaccaccaactccagcctacactagcaacaactcagcacgactcagagaaggccccatcttccccgcaccctccaagagcactg
gggcaaggcaccactctcacagtctccaggctcctcaagctagacgacgaaggccccatcttccccgcaccctccaagagcactg
gggcacaggccctggcttgtgtgctgctactcgaaggactacttccccgaaccgtgacggtgtcgtggaactcaggcgccctgaccagcg
gcgtgcacacttccgggtgctctacagtcctcagcagtcctcagtggactctactactccctcagcagcgtggtgaccgtgccctccagcagcttggactctactact
gaacctacaatgcaacgtgaatcacaagcccagcaacaccaaggtggacaagaaagttgagcccaaatcttactgtggctgtcaa
tcgtcttcatctccgccatctgatgagcagttgaaatctggaactgcctctgttgtgtgcctgctgaataacttctatcccagagaggccaa
agtacagtgaaggtggataacgcctccaatcgggtaactccaacagacagagaaacagcaaccccaaggtcaagagcagcacctaca
gcctcagcagcaccctgaccctgagcaaagcagactacgagaaacacaaagtctacgcctgcgaagtcacccatcagggcctgagc
tcgcccgtcacaaagagcttcaacaggggagagtgttaa-3'

Figure 16B

Amino acid sequence (SEQ ID No.:16)

N term-
MGWSYIILFLVATATDGHSQVQLQQPGTELVKPGASVKLSCKASGYTFTSYWIHWVKQRPGQGLE
WIGEINPSSGRTNYNEKFKNKVTVTVDKSSTTAYMQLSNLTSEDSAVYYCASRGYWGQGTTLTVS
SASTKGPSVFPLAPSSKSTSGGTAALGCLVKDYFPEPVTVSWNSGALTSGVHTFPAVLQSSGLYS
LSSVVTVPSSSLGTQTYICNVNHKPSNTKVDKKVEPKSCTVAAPSVFIFPPSDEQLKSGTASVVCL
LNNFYPREAKVQWKVDNALQSGNSQESVTEQDSKDSTYSLSSTLTLSKADYEKHKVYACEVTHQ
GLSSPVTKSFNRGEC- C term

Figure 17A

Nucleotide sequence (SEQ ID No.:11)

VL

5'-gacattgtgctgacccaatctccagctctttggctgtgtctctaggccagagggccaccatctctgcaaggccagcagtgttgatt
atgatggtggtagttatatgagttggttccaagacagaccaagggccagcagccaccaaatctcctgatctctgcatccaacttgaatcgg
catccagccagttatggcagtggctctggagactcacctcacctcaatatcatctctggagaggagagatgtgcaactatta
ctgtcagcaaagttatgaagaccccactcacgttcggtgctggtaccaaggtggagatcaaacga-3'

Figure 17B

Amino acid sequence (SEQ ID No.:12)

N term-

DIVLTQSPASLAVSLGQRATISCKASQSVDYDGGSYMSWFQQRPGQPPKLLISAASNLESGIPAR

FSGSGSGTDFTLNIHPVEEEDVATYYCQQSYEDPLTFGAGTKVEIKR- C term

Nucleotide sequence (SEQ ID No.: 3)

5'-ggtccaactgcaacagcctgaactgaagcctggagcctgggcttcagtgaagctgtcctgcaaggcttctggctacaccttcaccagttac
<u>CDRH1</u>
tggatacactgggtgaagcagaggcctggacaaggccttgagtggattgagagaattaatcctagtagtggtagtactaactacaatgaga
<u>CDRH2</u>
aattcaagaacaaggtcacagtgactgtagacaaatcttccaccacagccatccaatgcaactcagccactctgactgaggactctgggtct
attactgt<u>gcaagtagggggtactggggccaagctcacagtctctca</u>-3'
<u>CDRH3</u>

Figure 18B

Amino acid sequence (SEQ ID No.:4)

N term-
QVQLQQPGTELVKPGASVKLSCKASGYTFTSYWIHWVKQRPGQGLEWIGEINPSSGRTNYNEKFKN
         <u>CDRH1</u>                     <u>CDRH2</u>

KVTVTVDKSSTTAMQLSNLTSEDSAVYYCA<u>SRGY</u>WGQGTTLTVSS-C term
                              <u>CDRH3</u>

SEQUENCE LISTING

```
<160> NUMBER OF SEQ ID NOS: 30

<210> SEQ ID NO 1
<211> LENGTH: 1155
<212> TYPE: DNA
<213> ORGANISM: artificial
<220> FEATURE:
<223> OTHER INFORMATION: DCD-MvDN30.1 heavy chain

<400> SEQUENCE: 1
atgggatgga gctatatcat cctcttttg  gtagcaacag  ctacagatgg  ccactcccag      60
gtccaactgc aacagcctgg gactgaactg  gtgaagcctg  gggcttcagt  gaagctgtcc     120
tgcaaggctt ctggctacac cttcaccagt  tactggatac  actgggtgaa  gcagaggcct     180
ggacaaggcc ttgagtggat tggagagatt  aatcctagca  gcggtcgtac  taactacaac     240
gagaaattca agaacaaggt cacagtgact  gtagacaaat  cttccaccac  agcctacatg     300
```

```
caactcagca acctgacatc tgaggactct gcggtctatt actgtgcaag taggggctac    360
tggggccaag gcaccactct cacagtctcc tcagctagca cgaagggccc atcggtcttc    420
cccctggcac cctcctccaa gagcacctct ggggcacag cggccctggg ctgcctggtc     480
aaggactact tccccgaacc ggtgacggtg tcgtggaact caggcgccct gaccagcggc    540
gtgcacacct tccggctgt cctacagtcc tcaggactct actccctcag cagcgtggtg     600
accgtgccct ccagcagctt gggcacccag acctacatct gcaacgtgaa tcacaagccc    660
agcaacacca aggtggacaa gaaagttgag cccaaatctt gtgcaagcac gaagggccca    720
tcggtcttcc cctggcacc ctcctccaag agcacctctg gggcacagc ggccctgggc      780 tgcctggtca aggactactt ccccgaaccg gtgacggtgt cgtggaactc aggcgccctg    840
accagcggcg tgcacacctt cccggctgtc ctacagtcct caggactcta ctccctcagc    900
agcgtggtga ccgtgccctc agcagcttg gcacccaga cctacatctg caacgtgaat      960
cacaagccca gcaacaccaa ggtggacaag aaagttgagc ccaaatcttg tgacaaaact    1020
cacacaggtg ccgcatggag ccaccccag ttcgaaaaag gggccgcatg gagccacccc     1080
cagttcgaaa aggggccgc atggagccac ccccagttcg aaaaggggc cgcacaccat      1140 caccatcacc attag                                                   1155
```

<210> SEQ ID NO 2
<211> LENGTH: 384
<212> TYPE: PRT
<213> ORGANISM: artificial
<220> FEATURE:
<223> OTHER INFORMATION: DCD-MvDN30.1 heavy chain aa

<400> SEQUENCE: 2

```
Met Gly Trp Ser Tyr Ile Ile Leu Phe Leu Val Ala Thr Ala Thr Asp
1               5                   10                  15

Gly His Ser Gln Val Gln Leu Gln Gln Pro Gly Thr Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Ile His Trp Val Lys Gln Arg Pro Gly Gln Gly Leu
    50                  55                  60

Glu Trp Ile Gly Glu Ile Asn Pro Ser Gly Arg Thr Asn Tyr Asn
65                  70                  75                  80

Glu Lys Phe Lys Asn Lys Val Thr Val Thr Val Asp Lys Ser Ser Thr
                85                  90                  95

Thr Ala Tyr Met Gln Leu Ser Asn Leu Thr Ser Glu Asp Ser Ala Val
            100                 105                 110

Tyr Tyr Cys Ala Ser Arg Gly Tyr Trp Gly Gln Gly Thr Thr Leu Thr
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205
```

Thr Gln Thr Tyr Ile Cys Asn Val Asn His Lys Pro Ser Asn Thr Lys
        210                 215                 220

Val Asp Lys Lys Val Glu Pro Lys Ser Cys Ala Ser Thr Lys Gly Pro
225                 230                 235                 240

Ser Val Phe Pro Leu Ala Pro Ser Ser Lys Ser Thr Ser Gly Gly Thr
                245                 250                 255

Ala Ala Leu Gly Cys Leu Val Lys Asp Tyr Phe Pro Glu Pro Val Thr
            260                 265                 270

Val Ser Trp Asn Ser Gly Ala Leu Thr Ser Gly Val His Thr Phe Pro
        275                 280                 285

Ala Val Leu Gln Ser Ser Gly Leu Tyr Ser Leu Ser Ser Val Val Thr
    290                 295                 300

Val Pro Ser Ser Ser Leu Gly Thr Gln Thr Tyr Ile Cys Asn Val Asn
305                 310                 315                 320

His Lys Pro Ser Asn Thr Lys Val Asp Lys Lys Val Glu Pro Lys Ser
                325                 330                 335

Cys Asp Lys Thr His Thr Gly Ala Ala Trp Ser His Pro Gln Phe Glu
            340                 345                 350

Lys Gly Ala Ala Trp Ser His Pro Gln Phe Glu Lys Gly Ala Ala Trp
        355                 360                 365

Ser His Pro Gln Phe Glu Lys Gly Ala Ala His His His His His His
    370                 375                 380

<210> SEQ ID NO 3
<211> LENGTH: 334
<212> TYPE: DNA
<213> ORGANISM: artificial
<220> FEATURE:
<223> OTHER INFORMATION: DN30 VH domain

<400> SEQUENCE: 3

```
ggtccaactg caacagcctg ggactgaact ggtgaagcct ggggcttcag tgaagctgtc     60
ctgcaaggct tctggctaca ccttcaccag ttactggata cactgggtga agcagaggcc    120
tggacaaggc cttgagtgga ttggagagat taatcctagc agcggtcgta ctaactacaa    180
cgagaaattc aagaacaagg tcacagtgac tgtagacaaa tcttccacca cagcctacat    240
gcaactcagc aacctgacat ctgaggactc tgcggtctat tactgtgcaa gtaggggcta    300
ctggggccaa ggcaccactc tcacagtctc ctca                                334
```

<210> SEQ ID NO 4
<211> LENGTH: 112
<212> TYPE: PRT
<213> ORGANISM: artificial
<220> FEATURE:
<223> OTHER INFORMATION: DN30 VH domain aa

<400> SEQUENCE: 4

Gln Val Gln Leu Gln Gln Pro Gly Thr Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile His Trp Val Lys Gln Arg Pro Gly Gln Gly Leu Glu Trp Ile
        35                  40                  45

Gly Glu Ile Asn Pro Ser Ser Gly Arg Thr Asn Tyr Asn Glu Lys Phe
    50                  55                  60

Lys Asn Lys Val Thr Val Thr Val Asp Lys Ser Ser Thr Thr Ala Tyr

```
                65                  70                  75                  80
Met Gln Leu Ser Asn Leu Thr Ser Glu Asp Ser Ala Val Tyr Tyr Cys
                    85                  90                  95

Ala Ser Arg Gly Tyr Trp Gly Gln Gly Thr Thr Leu Thr Val Ser Ser
                100                 105                 110

<210> SEQ ID NO 5
<211> LENGTH: 315
<212> TYPE: DNA
<213> ORGANISM: artificial
<220> FEATURE:
<223> OTHER INFORMATION: human CH1 domain

<400> SEQUENCE: 5
aagggcccat cggtcttccc cctggcaccc tcctccaaga gcacctctgg gggcacagcg      60
gccctgggct gcctggtcaa ggactacttc cccgaaccgg tgacggtgtc gtggaactca     120
ggcgccctga ccagcggcgt gcacaccttc ccggctgtcc tacagtcctc aggactctac     180
tccctcagca gcgtggtgac cgtgccctcc agcagcttgg gcacccagac ctacatctgc     240
aacgtgaatc acaagcccag caacaccaag gtggacaaga agttgagcc caaatcttgt      300 gacaaaactc acaca                                                      315

<210> SEQ ID NO 6
<211> LENGTH: 105
<212> TYPE: PRT
<213> ORGANISM: artificial
<220> FEATURE:
<223> OTHER INFORMATION: human CH1 domain aa

<400> SEQUENCE: 6

Lys Gly Pro Ser Val Phe Pro Leu Ala Pro Ser Ser Lys Ser Thr Ser
1               5                   10                  15

Gly Gly Thr Ala Ala Leu Gly Cys Leu Val Lys Asp Tyr Phe Pro Glu
                20                  25                  30

Pro Val Thr Val Ser Trp Asn Ser Gly Ala Leu Thr Ser Gly Val His
            35                  40                  45

Thr Phe Pro Ala Val Leu Gln Ser Ser Gly Leu Tyr Ser Leu Ser Ser
        50                  55                  60

Val Val Thr Val Pro Ser Ser Ser Leu Gly Thr Gln Thr Tyr Ile Cys
65                  70                  75                  80

Asn Val Asn His Lys Pro Ser Asn Thr Lys Val Asp Lys Lys Val Glu
                85                  90                  95

Pro Lys Ser Cys Asp Lys Thr His Thr
                100                 105

<210> SEQ ID NO 7
<211> LENGTH: 108
<212> TYPE: DNA
<213> ORGANISM: artificial
<220> FEATURE:
<223> OTHER INFORMATION: strep tag

<400> SEQUENCE: 7
ggtgccgcat ggagccaccc ccagttcgaa aaaggggccg catggagcca ccccagttc       60 gaaaaagggg ccgcatggag ccaccccag ttcgaaaaag gggccgca                   108

<210> SEQ ID NO 8
<211> LENGTH: 18
<212> TYPE: DNA
```

```
<213> ORGANISM: artificial
<220> FEATURE:
<223> OTHER INFORMATION: polyhis tag

<400> SEQUENCE: 8
caccatcacc atcaccat                                                       18

<210> SEQ ID NO 9
<211> LENGTH: 1035
<212> TYPE: DNA
<213> ORGANISM: artificial
<220> FEATURE:
<223> OTHER INFORMATION: DCD-MvDN30.1 light chain

<400> SEQUENCE: 9
atggagacag acacaatcct gctatgggtg ctgctgctct gggttccagg ctccactggt         60
gacattgtgc tgacccaatc tccagcttct ttggctgtgt ctctagggca gagggccacc        120
atctcctgca aggccagcca aagtgttgat tatgatggtg gtagttatat gagttggttc        180
caacagagac aggacagcc acccaaactc ctcatctctg ctgcatccaa ccttgaatct         240
ggcatcccag ccaggtttag tggcagtggc tctgggacag acttcaccct caatatccat        300
cctgtggagg aggaggatgt tgcaacctat tactgtcagc aaagttatga agacccgctc        360
acgttcggtg ctggtaccaa ggtggagatc aaacgaactg tggctgcacc atctgtcttc        420
atcttcccgc catctgatga gcagttgaaa tctggaactg cctctgttgt gtgcctgctg        480
aataacttct atcccagaga ggccaaagta cagtggaagg tggataacgc cctccaatcg        540
ggtaactccc aggagagtgt cacagagcag gacagcaagg acagcaccta cagcctcagc        600
agcaccctga cgctgagcaa agcagactac gagaaacaca agtctacgc ctgcgaagtc         660 acccatcagg gcctgagctc gcccgtcaca aagagcttca caggggaga gtgtactgtg         720 gctgcaccat ctgtcttcat cttcccgcca tctgatgagc agttgaaatc tggaactgcc        780
tctgttgtgt gcctgctgaa taacttctat cccagagagg ccaaagtaca gtggaaggtg        840
gataacgccc tccaatcggg taactcccag gagagtgtca cagagcagga cagcaaggac        900
agcacctaca gcctcagcag caccctgacg ctgagcaaag cagactacga gaaacacaaa        960
gtctacgcct gcgaagtcac ccatcagggc ctgagctcgc ccgtcacaaa gagcttcaac       1020
aggggagagt gttaa                                                        1035

<210> SEQ ID NO 10
<211> LENGTH: 344
<212> TYPE: PRT
<213> ORGANISM: artificial
<220> FEATURE:
<223> OTHER INFORMATION: DCD-MvDN30.1 light chain aa

<400> SEQUENCE: 10

Met Glu Thr Asp Thr Ile Leu Leu Trp Val Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Lys Ala Ser Gln Ser
        35                  40                  45

Val Asp Tyr Asp Gly Gly Ser Tyr Met Ser Trp Phe Gln Gln Arg Pro
    50                  55                  60

Gly Gln Pro Pro Lys Leu Leu Ile Ser Ala Ala Ser Asn Leu Glu Ser
65                  70                  75                  80
```

```
Gly Ile Pro Ala Arg Phe Ser Gly Ser Gly Ser Gly Thr Asp Phe Thr
                85                  90                  95
Leu Asn Ile His Pro Val Glu Glu Asp Val Ala Thr Tyr Tyr Cys
            100                 105                 110
Gln Gln Ser Tyr Glu Asp Pro Leu Thr Phe Gly Ala Gly Thr Lys Val
        115                 120                 125
Glu Ile Lys Arg Thr Val Ala Ala Pro Ser Val Phe Ile Phe Pro Pro
    130                 135                 140
Ser Asp Glu Gln Leu Lys Ser Gly Thr Ala Ser Val Val Cys Leu Leu
145                 150                 155                 160
Asn Asn Phe Tyr Pro Arg Glu Ala Lys Val Gln Trp Lys Val Asp Asn
                165                 170                 175
Ala Leu Gln Ser Gly Asn Ser Gln Glu Ser Val Thr Glu Gln Asp Ser
            180                 185                 190
Lys Asp Ser Thr Tyr Ser Leu Ser Ser Thr Leu Thr Leu Ser Lys Ala
        195                 200                 205
Asp Tyr Glu Lys His Lys Val Tyr Ala Cys Glu Val Thr His Gln Gly
    210                 215                 220
Leu Ser Ser Pro Val Thr Lys Ser Phe Asn Arg Gly Glu Cys Thr Val
225                 230                 235                 240
Ala Ala Pro Ser Val Phe Ile Phe Pro Pro Ser Asp Glu Gln Leu Lys
                245                 250                 255
Ser Gly Thr Ala Ser Val Val Cys Leu Leu Asn Asn Phe Tyr Pro Arg
            260                 265                 270
Glu Ala Lys Val Gln Trp Lys Val Asp Asn Ala Leu Gln Ser Gly Asn
        275                 280                 285
Ser Gln Glu Ser Val Thr Glu Gln Asp Ser Lys Asp Ser Thr Tyr Ser
    290                 295                 300
Leu Ser Ser Thr Leu Thr Leu Ser Lys Ala Asp Tyr Glu Lys His Lys
305                 310                 315                 320
Val Tyr Ala Cys Glu Val Thr His Gln Gly Leu Ser Ser Pro Val Thr
                325                 330                 335
Lys Ser Phe Asn Arg Gly Glu Cys
            340

<210> SEQ ID NO 11
<211> LENGTH: 336
<212> TYPE: DNA
<213> ORGANISM: artificial
<220> FEATURE:
<223> OTHER INFORMATION: DN30 VL domain

<400> SEQUENCE: 11
gacattgtgc tgacccaatc tccagcttct ttggctgtgt ctctagggca gagggccacc      60
atctcctgca aggccagcca aagtgttgat tatgatggtg gtagttatat gagttggttc     120
caacagagac caggacagcc acccaaactc ctcatctctg ctgcatccaa ccttgaatct     180
ggcatcccag ccaggtttag tggcagtggc tctgggacag acttcaccct caatatccat     240
cctgtggagg aggaggatgt tgcaacctat tactgtcagc aaagttatga agacccgctc     300
acgttcggtg ctggtaccaa ggtggagatc aaacga                               336

<210> SEQ ID NO 12
<211> LENGTH: 112
<212> TYPE: PRT
<213> ORGANISM: artificial
<220> FEATURE:
```

<223> OTHER INFORMATION: DN30 VL domain aa

<400> SEQUENCE: 12

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Gly Ser Tyr Met Ser Trp Phe Gln Gln Arg Pro Gly Gln Pro Pro
        35                  40                  45

Lys Leu Leu Ile Ser Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Val Ala Thr Tyr Tyr Cys Gln Gln Ser Tyr
                85                  90                  95

Glu Asp Pro Leu Thr Phe Gly Ala Gly Thr Lys Val Glu Ile Lys Arg
            100                 105                 110

<210> SEQ ID NO 13
<211> LENGTH: 318
<212> TYPE: DNA
<213> ORGANISM: artificial
<220> FEATURE:
<223> OTHER INFORMATION: human CL domain

<400> SEQUENCE: 13
actgtggctg caccatctgt cttcatcttc ccgccatctg atgagcagtt gaaatctgga      60
actgcctctg ttgtgtgcct gctgaataac ttctatccca gagaggccaa agtacagtgg     120
aaggtggata acgccctcca atcgggtaac tcccaggaga gtgtcacaga gcaggacagc     180
aaggacagca cctacagcct cagcagcacc ctgacgctga gcaaagcaga ctacgagaaa     240
cacaaagtct acgcctgcga agtcacccat cagggcctga gctcgcccgt cacaaagagc     300
ttcaacaggg gagagtgt                                                   318

<210> SEQ ID NO 14
<211> LENGTH: 106
<212> TYPE: PRT
<213> ORGANISM: artificial
<220> FEATURE:
<223> OTHER INFORMATION: human CL domain aa

<400> SEQUENCE: 14

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

```
<210> SEQ ID NO 15
<211> LENGTH: 1023
<212> TYPE: DNA
<213> ORGANISM: artificial
<220> FEATURE:
<223> OTHER INFORMATION: DCD-MvDN30.2 heavy chain

<400> SEQUENCE: 15
```

| | | |
|---|---|---|
| atgggatgga gctatatcat cctcttttg gtagcaacag ctacagatgg ccactcccag | 60 |
| gtccaactgc aacagcctgg gactgaactg gtgaagcctg gggcttcagt gaagctgtcc | 120 |
| tgcaaggctt ctggctacac cttcaccagt tactggatac actgggtgaa gcagaggcct | 180 |
| ggacaaggcc ttgagtggat tggagagatt aatcctagca gcggtcgtac taactacaac | 240 |
| gagaaattca agaacaaggt cacagtgact gtagacaaat cttccaccac agcctacatg | 300 |
| caactcagca acctgacatc tgaggactct gcggtctatt actgtgcaag taggggctac | 360 |
| tggggccaag gcaccactct cacagtctcc tcagctagca cgaagggccc atcggtcttc | 420 |
| cccctggcac cctcctccaa gagcacctct gggggcacag cggccctggg ctgcctggtc | 480 |
| aaggactact ccccgaacc ggtgacggtg tcgtggaact caggcgccct gaccagcggc | 540 |
| gtgcacacct tccggctgt cctacagtcc tcaggactct actccctcag cagcgtggtg | 600 |
| accgtgccct ccagcagctt gggcacccag acctacatct gcaacgtgaa tcacaagccc | 660 |
| agcaacacca aggtggacaa gaaagttgag cccaaatctt gtactgtggc tgcaccatct | 720 |
| gtcttcatct tccgccatc tgatgagcag ttgaaatctg gaactgcctc tgttgtgtgc | 780 |
| ctgctgaata acttctatcc cagagaggcc aaagtacagt ggaaggtgga taacgccctc | 840 |
| caatcgggta actcccagga gagtgtcaca gagcaggaca gcaaggacag cacctacagc | 900 |
| ctcagcagca ccctgacgct gagcaaagca gactacgaga acacaaaagt ctacgcctgc | 960 |
| gaagtcaccc atcagggcct gagctcgccc gtcacaaaga gcttcaacag gggagagtgt | 1020 |
| taa | 1023 |

```
<210> SEQ ID NO 16
<211> LENGTH: 340
<212> TYPE: PRT
<213> ORGANISM: artificial
<220> FEATURE:
<223> OTHER INFORMATION: DCD-MvDN30.2 heavy chain aa

<400> SEQUENCE: 16
```

Met Gly Trp Ser Tyr Ile Ile Leu Phe Leu Val Ala Thr Ala Thr Asp
1               5                   10                  15

Gly His Ser Gln Val Gln Leu Gln Gln Pro Gly Thr Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Ile His Trp Val Lys Gln Arg Pro Gly Gln Gly Leu
    50                  55                  60

Glu Trp Ile Gly Glu Ile Asn Pro Ser Ser Gly Arg Thr Asn Tyr Asn
65                  70                  75                  80

Glu Lys Phe Lys Asn Lys Val Thr Val Thr Val Asp Lys Ser Ser Thr
                85                  90                  95

Thr Ala Tyr Met Gln Leu Ser Asn Leu Thr Ser Glu Asp Ser Ala Val
            100                 105                 110

Tyr Tyr Cys Ala Ser Arg Gly Tyr Trp Gly Gln Gly Thr Thr Leu Thr
        115                 120                 125

Val Ser Ser Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
        195                 200                 205

Thr Gln Thr Tyr Ile Cys Asn Val Asn His Lys Pro Ser Asn Thr Lys
    210                 215                 220

Val Asp Lys Lys Val Glu Pro Lys Ser Cys Thr Val Ala Ala Pro Ser
225                 230                 235                 240

Val Phe Ile Phe Pro Pro Ser Asp Glu Gln Leu Lys Ser Gly Thr Ala
                245                 250                 255

Ser Val Val Cys Leu Leu Asn Asn Phe Tyr Pro Arg Glu Ala Lys Val
            260                 265                 270

Gln Trp Lys Val Asp Asn Ala Leu Gln Ser Gly Asn Ser Gln Glu Ser
        275                 280                 285

Val Thr Glu Gln Asp Ser Lys Asp Ser Thr Tyr Ser Leu Ser Ser Thr
    290                 295                 300

Leu Thr Leu Ser Lys Ala Asp Tyr Glu Lys His Lys Val Tyr Ala Cys
305                 310                 315                 320

Glu Val Thr His Gln Gly Leu Ser Ser Pro Val Thr Lys Ser Phe Asn
                325                 330                 335

Arg Gly Glu Cys
            340

<210> SEQ ID NO 17
<211> LENGTH: 1167
<212> TYPE: DNA
<213> ORGANISM: artificial
<220> FEATURE:
<223> OTHER INFORMATION: DCD-MvDN30.2 light chain

<400> SEQUENCE: 17
atggagacag acacaatcct gctatgggtg ctgctgctct ggttccagg  ctccactggt      60 gacattgtgc tgacccaatc tccagcttct ttggctgtgt ctctagggca gagggccacc     120
atctcctgca aggccagcca aagtgttgat tatgatggtg gtagttatat gagttggttc     180
caacagagac aggacagcc  acccaaactc ctcatctctg ctgcatccaa ccttgaatct     240
ggcatcccag ccaggtttag tggcagtggc tctgggacag acttcaccct caatatccat     300
cctgtggagg aggaggatgt tgcaacctat tactgtcagc aaagttatga agaccgctc      360 acgttcggtg ctggtaccaa ggtggagatc aaacgaactg tggctgcacc atctgtcttc     420
atcttcccgc catctgatga gcagttgaaa tctggaactg cctctgttgt gtgcctgctg     480
aataacttct atcccagaga ggccaaagta cagtggaagg tggataacgc cctccaatcg     540
ggtaactccc aggagagtgt cacagagcag gacagcaagg acagcaccta cagcctcagc     600
agcaccctga cgctgagcaa agcagactac gagaaacaca agtctacgc  ctgcgaagtc     660 acccatcagg gcctgagctc gcccgtcaca aagagcttca caggggaga  gtgtgcaagc     720 acgaagggcc atcggtcttc ccccctggca ccctcctcca agagcacctc tgggggcaca     780
gcggccctgg gctgcctggt caaggactac ttccccgaac cggtgacggt gtcgtggaac     840

```
tcaggcgccc tgaccagcgg cgtgcacacc ttcccggctg tcctacagtc ctcaggactc    900
tactccctca gcagcgtggt gaccgtgccc tccagcagct gggcaccca gacctacatc    960 tgcaacgtga atcacaagcc cagcaacacc aaggtggaca agaaagttga gcccaaatct   1020
tgtgacaaaa ctcacacagg tgccgcatgg agccaccccc agttcgaaaa aggggccgca   1080
tggagccacc cccagttcga aaaggggcc gcatggagcc accccagtt cgaaaaaggg    1140 gccgcacacc atcaccatca ccattag                                       1167
```

<210> SEQ ID NO 18
<211> LENGTH: 388
<212> TYPE: PRT
<213> ORGANISM: artificial
<220> FEATURE:
<223> OTHER INFORMATION: DCD-MvDN30.2 light chain aa

<400> SEQUENCE: 18

```
Met Glu Thr Asp Thr Ile Leu Leu Trp Val Leu Leu Trp Val Pro
 1               5                  10                  15

Gly Ser Thr Gly Asp Ile Val Leu Thr Gln Ser Pro Ala Ser Leu Ala
             20                  25                  30

Val Ser Leu Gly Gln Arg Ala Thr Ile Ser Cys Lys Ala Ser Gln Ser
         35                  40                  45

Val Asp Tyr Asp Gly Gly Ser Tyr Met Ser Trp Phe Gln Gln Arg Pro
     50                  55                  60

Gly Gln Pro Pro Lys Leu Leu Ile Ser Ala Ala Ser Asn Leu Glu Ser
 65                  70                  75                  80

Gly Ile Pro Ala Arg Phe Ser Gly Ser Gly Ser Gly Thr Asp Phe Thr
                 85                  90                  95

Leu Asn Ile His Pro Val Glu Glu Asp Val Ala Thr Tyr Tyr Cys
             100                 105                 110

Gln Gln Ser Tyr Glu Asp Pro Leu Thr Phe Gly Ala Gly Thr Lys Val
         115                 120                 125

Glu Ile Lys Arg Thr Val Ala Ala Pro Ser Val Phe Ile Phe Pro Pro
     130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys Ala Ser
225                 230                 235                 240

Thr Lys Gly Pro Ser Val Phe Pro Leu Ala Pro Ser Ser Lys Ser Thr
                245                 250                 255

Ser Gly Gly Thr Ala Ala Leu Gly Cys Leu Val Lys Asp Tyr Phe Pro
            260                 265                 270

Glu Pro Val Thr Val Ser Trp Asn Ser Gly Ala Leu Thr Ser Gly Val
        275                 280                 285

His Thr Phe Pro Ala Val Leu Gln Ser Ser Gly Leu Tyr Ser Leu Ser
    290                 295                 300
```

```
Ser Val Val Thr Val Pro Ser Ser Leu Gly Thr Gln Thr Tyr Ile
305                 310                 315                 320

Cys Asn Val Asn His Lys Pro Ser Asn Thr Lys Val Asp Lys Lys Val
            325                 330                 335

Glu Pro Lys Ser Cys Asp Lys Thr His Thr Gly Ala Ala Trp Ser His
        340                 345                 350

Pro Gln Phe Glu Lys Gly Ala Ala Trp Ser His Pro Gln Phe Glu Lys
        355                 360                 365

Gly Ala Ala Trp Ser His Pro Gln Phe Glu Lys Gly Ala Ala His His
    370                 375                 380

His His His His
385

<210> SEQ ID NO 19
<211> LENGTH: 8
<212> TYPE: PRT
<213> ORGANISM: artificial
<220> FEATURE:
<223> OTHER INFORMATION: DN30 CDRH1 aa

<400> SEQUENCE: 19

Gly Tyr Thr Phe Thr Ser Tyr Trp
1               5

<210> SEQ ID NO 20
<211> LENGTH: 24
<212> TYPE: DNA
<213> ORGANISM: artificial
<220> FEATURE:
<223> OTHER INFORMATION: DN30 CDRH1

<400> SEQUENCE: 20
ggctacacct tcaccagtta ctgg                                          24

<210> SEQ ID NO 21
<211> LENGTH: 8
<212> TYPE: PRT
<213> ORGANISM: artificial
<220> FEATURE:
<223> OTHER INFORMATION: DN30 CDRH2 aa

<400> SEQUENCE: 21

Ile Asn Pro Ser Ser Gly Arg Thr
1               5

<210> SEQ ID NO 22
<211> LENGTH: 24
<212> TYPE: DNA
<213> ORGANISM: artificial
<220> FEATURE:
<223> OTHER INFORMATION: DN30 CDRH2

<400> SEQUENCE: 22
attaatccta gcagcggtcg tact                                          24

<210> SEQ ID NO 23
<211> LENGTH: 5
<212> TYPE: PRT
<213> ORGANISM: artificial
<220> FEATURE:
<223> OTHER INFORMATION: DN30 CDRH3 aa

<400> SEQUENCE: 23
```

Ala Ser Arg Gly Tyr
1               5

<210> SEQ ID NO 24
<211> LENGTH: 15
<212> TYPE: DNA
<213> ORGANISM: artificial
<220> FEATURE:
<223> OTHER INFORMATION: DN30 CDRH3

<400> SEQUENCE: 24
gcaagtaggg gctac                                                15

<210> SEQ ID NO 25
<211> LENGTH: 10
<212> TYPE: PRT
<213> ORGANISM: artificial
<220> FEATURE:
<223> OTHER INFORMATION: DN30 CDRL1 aa

<400> SEQUENCE: 25

Gln Ser Val Asp Tyr Asp Gly Gly Ser Tyr
1               5                   10

<210> SEQ ID NO 26
<211> LENGTH: 30
<212> TYPE: DNA
<213> ORGANISM: artificial
<220> FEATURE:
<223> OTHER INFORMATION: DN30 CDRL1

<400> SEQUENCE: 26
caaagtgttg attatgatgg tggtagttat                                30

<210> SEQ ID NO 27
<211> LENGTH: 3
<212> TYPE: PRT
<213> ORGANISM: artificial
<220> FEATURE:
<223> OTHER INFORMATION: DN30 CDRL2 aa

<400> SEQUENCE: 27

Ala Ala Ser
1

<210> SEQ ID NO 28
<211> LENGTH: 9
<212> TYPE: DNA
<213> ORGANISM: artificial
<220> FEATURE:
<223> OTHER INFORMATION: DN30 CDRL2

<400> SEQUENCE: 28 gctgcatcc                                                        9

<210> SEQ ID NO 29
<211> LENGTH: 9
<212> TYPE: PRT
<213> ORGANISM: artificial
<220> FEATURE:
<223> OTHER INFORMATION: DN30 CDRL3 aa

<400> SEQUENCE: 29

Gln Gln Ser Tyr Glu Asp Pro Leu Thr
1               5

```
<210> SEQ ID NO 30
<211> LENGTH: 27
<212> TYPE: DNA
<213> ORGANISM: artificial
<220> FEATURE:
<223> OTHER INFORMATION: DN30 CDRL3 aa

<400> SEQUENCE: 30
cagcaaagtt atgaagaccc gctcacg                                        27
```

ANTIBODY FRAGMENTS, COMPOSITIONS AND USES THEREOF

CROSS-REFERENCE TO RELATED APPLICATIONS

This application is a divisional of U.S. application Ser. No. 14/758,079 filed on Jun. 26, 2015, which is a 371 U.S. national phase of International Application Serial No. PCT/IB2014/058098, filed Jan. 7, 2014, which claims the benefit of priority from Italian Patent Application Serial No. TO2013A000012, filed Jan. 9, 2013, the contents of each of which are incorporated herein by reference.

FIELD OF THE INVENTION

The present disclosure concerns new antibody fragments with improved in vivo stability.

BACKGROUND

Targeted therapy, the new frontier of cancer treatment, employs pharmacological tools (drugs or antibodies) specifically blocking crucial gene products that sustain the transformed phenotype. Currently, cancer targeted therapy is employed in the clinic for the treatment of chronic myelogenous leukemias (CML), addicted to the tyrosine kinase molecule ABL, for the treatment of a subset of Non-Small Cell Lung Cancers (NSCLC) and Colon-Rectum Carcinomas (CRC) relying on Epidermal Growth Factor Receptor (EGFR/HER-1) activation and for the treatment of BRAF-dependent melanomas.

Receptors with tyrosine kinase activity (RTKs) are interesting candidates for targeted therapy as they are often hyper-activated in several types of tumors. They can be inhibited by different types of targeting molecules, such as antibodies, that upon interaction with the extracellular part of the receptor are able to perturb the receptor-induced intracellular signaling, and chemically-synthesized small molecules that interfere with the receptor catalytic activity.

Among the different RTKs, the product of the c-met proto-oncogene, the Hepatocyte Growth Factor Receptor (HGFR/Met), is emerging as one of the most important activated oncogene in cancer. Met controls a genetic program known as 'invasive growth' that includes pro-mitogenic, pro-invasive and anti-apotoptic cues. Through these physiological signals, Met provides with a better fitness the tumor, helping it to overcome selective barriers in cancer progression. Moreover Met sustains tumor growth by its ability to promote tumor angiogenesis. In the last years, Met also resulted responsible for the aggressiveness developed by tumors treated with anti-angiogenic agents and for resistance to conventional radiotherapy. Additionally, MET gene alteration can be a primary cause of transformation, in all of those cases in which it has been genetically selected for the long term maintenance of the primary transformed phenotype.

All the above listed findings have prompted the development of several molecules suitable to inhibit Met signaling, including competitive inhibitors of HGF, chemical Met kinase inhibitors, anti-HGF and anti-Met antibodies. Some of these molecules, until now, have been tested only for research purpose. Clinical trials are currently ongoing with neutralizing anti-HGF antibodies, anti-Met antibodies and several small molecules.

From several view-points, an anti-Met antibody able to inhibit Met signaling would be preferable. Antibodies are highly specific, stable and, thank to their natural design, they are generally well tolerated by the host. In the last years, several efforts have been put to generate therapeutic anti-Met antibodies. However, a lot of failures have been registered, as the majority of the anti-Met antibodies behave as agonists, mimicking the HGF action. This is mostly due to the fact that, thanks to their bivalent structure, antibodies can stabilize receptor dimers, allowing trans-phosphorylation of Met, with its consequent activation. In one case, an agonist anti-Met antibody (5D5) has been engineered and converted in a monovalent form (One Armed-5D5) that, competing with HGF binding, is endowed with therapeutic potential (1,2). This molecule has been recently entered a phase III clinical trial for the treatment of a subset of Non Small Cell Lung Cancer patients, characterized by high level of Met expression in the tumors, in combination with erlotinib (3).

The monoclonal antibody DN30 is a mouse IgG2A directed against the extracellular moiety of the human Met receptor (4). It binds with sub-nanomolar affinity the fourth IPT domain of the Met receptor extracellular region. At the beginning, it was characterized as a partial agonist of Met, able to promote some, but not all, of the Met-mediated biological cell responses. Later it has been demonstrated that it can act as an inhibitor of tumor growth and metastasis through a mechanism of receptor 'shedding' (5). Receptor shedding is a physiologic cellular mechanism of protein degradation acting on diverse growth factors, cytokines, receptors and adhesion molecules. Met shedding is articulated in two steps: first a metalloprotease, the ADAM-10, cleaves the extracellular domain of Met recognizing a specific sequence localized immediately upstream to the trans-membrane region; then the remaining transmembrane fragment becomes substrate of a second protease ($\gamma$-secretase) that detaches the kinase-containing portion from the membrane and rapidly addresses it towards the proteasome degradation pathway (6,7). The enhancement of this mechanism exerted by the DN30 leads to a reduction in the number of Met receptors exposed at the cell surface. At the same time, it releases a soluble, 'decoy' ecto-domain in the extracellular space. The latter competes with the intact trans-membrane receptor for ligand binding and inhibits receptor homo-dimerization by forming hetero-dimeric complexes with bona fide Met. All these actions strongly impair Met-mediated signaling and result in prevention of the downstream biological effects.

Recently the present inventors demonstrated that the monovalent Fab fragment of the DN30 anti-Met monoclonal antibody (DN30 Fab) is cleared of any agonistic activity and maintains the ability to induce shedding, thus resulting in a potent Met inhibitor (8). Induction of Met shedding by DN30-Fab is dependent on the selective antibody-antigen interaction but is independent from receptor activation. This mechanism of action, based on the simple elimination of Met from the cell surface, gives to the DN30-Fab a strong advantage over other inhibitors, as it can be effective against all the forms of Met activation, whether HGF-dependent or not, induced by overexpression, mutation or gene amplification.

While the recombinant DN30-Fab is very attractive for clinical applications, the short Fab plasma half-life—mostly due to renal clearance—severely limits its use for patient treatment.

Currently, the most consolidated technique to improve the pharmacological properties of a Fab fragment is to increase its molecular weight by conjugation with Poly Ethylen Glycol (PEG). Fab PEGylation is a route pursued in most of the cases employing Fab in the clinic. The covalent attachment of the polymer chains to the antibody fragment, obtained efficiently and without loss of antigen binding properties, is not an obvious process and requires a strong effort of setting up.

Another technique used to improve the pharmacological properties of a Fab fragment is the one disclosed in EP-A-1 718 677. Such a procedure, used to generate the One Armed form of monoclonal antibody 5D5 commented above, is the production—on recombinant basis—of three different antibody chains in the same cell, the light chain (VL-CL), the heavy chain (VH-CH1-CH2-CH3) and the Fc portion of the heavy chain (CH2-CH3). The CH2-CH3 domains are not wild type: mutations, giving rise to specific tridimensional structures, are included. In one polypeptide, the CH2-CH3 region incorporates a sequence forming a protuberance, while in the other polypeptide the CH2-CH3 region contains a sequence forming a cavity, in which the protuberance can be inserted (Knob into hole structure). The presence of these tridimensional structures allows the preferable formation of heterodimers in which the heavy chain forms disulfide bonds with the Fc fragment, but does not exclude at all the formation of homodimers (i.e. two heavy chains linked together and two Fc linked together). Purification allowing the separation of the unwanted homodimers from the wanted heterodimers is mandatory. Thus the "One Armed procedure", although very elegant, is cumbersome as it requires additional steps in the overall process that complicate the manufacturing and reduce the yield of the recombinant antibody.

It is therefore felt the necessity of a different solution to increase Fab plasma half-life for in vivo therapeutic use.

SUMMARY OF THE INVENTION

The object of this disclosure is to provide an antibody fragment with improved in vivo stability.

According to the invention, the above object is achieved thanks to the subject matter recalled specifically in the ensuing claims, which are understood as forming an integral part of this disclosure.

An embodiment of the present disclosure provides an antibody fragment comprising a first polypeptide comprising a light chain variable domain and two constant domains and a second polypeptide comprising a heavy chain variable domain and two constant domains, wherein two chain constant domains are light chain constant domains and two constant domains are heavy chain CH1 constant domains, fused in different combinations to the variable domains.

A further embodiment of the present disclosure concerns an antibody fragment as defined above that is more stable in vivo than the Fab molecule comprising the light and heavy chain variable domains.

A still further embodiment concerns an antibody fragment as defined above that specifically binds the hepatocyte growth factor receptor (HGFR/Met).

BRIEF DESCRIPTION OF THE DRAWINGS

The invention will now be described in detail, purely by way of an illustrative and non-limiting example and, with reference to the accompanying drawings, wherein:

FIG. 1A SNU-5 a human gastric carcinoma cell line; FIG. 1B H1993-NC1 a non small cell lung carcinoma cell line. Cells were incubated for 48 hrs in serum free medium with the indicated concentrations of the two antibody fragments derived from DN30 mAb. Total Met levels were determined by Western blot analysis of cell extracts using anti-Met antibodies. The two Met bands correspond to the unprocessed (p190 Met) and mature (p145 Met) forms of the receptor. Met shedding was determined by Western blot analysis of conditioned medium using anti-Met antibodies. Both molecules efficiently induce Met-shedding/down-regulation.

FIG. 2A EBC-1 a non small cell lung carcinoma cell line; FIG. 2B Hs746T a human gastric carcinoma cell line. Cells were plated in 96 well dishes (1000/well) in 10% FCS medium. After 24 hrs cells were treated with increasing concentrations of antibodies for further 72 hrs. Number of cells was evaluated by Cell titer-glo (Perkin Elmer). Each point is the mean of triplicate values; bars represent standard deviation. Both molecules efficiently inhibit cell growth of Met-addicted cells.

FIGS. 10A-10D human gastric carcinoma cell lines; FIGS. 10E-10F non small cell lung carcinoma cell lines. Cells were plated in 96 well costar (1000/well) in 5% FCS medium. After 24 hrs cells were treated with increasing concentrations of the different molecules for further 72 hrs. Number of cells was evaluated by Cell titer-glo (Promega). The plots represent the percentage of alive cells respect to untreated control. Each point is the mean of triplicate values. The new molecules efficiently inhibit cell growth of Met-addicted cells.

FIGS. 13A-13B: Nucleotide and amino acid sequences of a first embodiment of a first polypeptide of an antibody fragment according to the present disclosure. The sequences correspond to the polypeptide derived from the light chain, VL-CL-CL. The CDR regions are underlined both in the nucleotide and amino acid sequences.

FIGS. 14A-14B: Nucleotide and amino acid sequences of a first embodiment of a second polypeptide of an antibody fragment according to the present disclosure. The sequences correspond to the polypeptide derived from the heavy chain, VH-CH1-CH1-TAGs. The CDR regions are underlined both in the nucleotide and amino acid sequences. Strep and Histidine TAGs in capital italic letters.

FIGS. 15A-15B: Nucleotide and amino acid sequences of a second embodiment of a first polypeptide of an antibody fragment according to the present disclosure. The sequences correspond to the polypeptide derived from the light chain, VL-CL-CH1-TAGs. The CDR regions are underlined both in the nucleotide and amino acid sequences. Strep and Histidine TAGs in capital italic letters.

FIGS. 16A-16B: Nucleotide and amino acid sequences of a second embodiment of a second polypeptide of an antibody fragment according to the present disclosure. The sequences correspond to the polypeptide derived from the heavy chain, VH-CH1-CL. The CDR regions are underlined both in the nucleotide and amino acid sequences.

FIGS. 17A-17B: Nucleotide and amino acid sequences of DN30 light chain variable domain. The CDR regions are underlined both in the nucleotide and amino acid sequences.

FIGS. 18A-18B: Nucleotide and amino acid sequences of DN30 heavy chain variable domain. The CDR regions are underlined both in the nucleotide and amino acid sequences.

DETAILED DESCRIPTION OF THE INVENTION

Figures 1A, 1B:
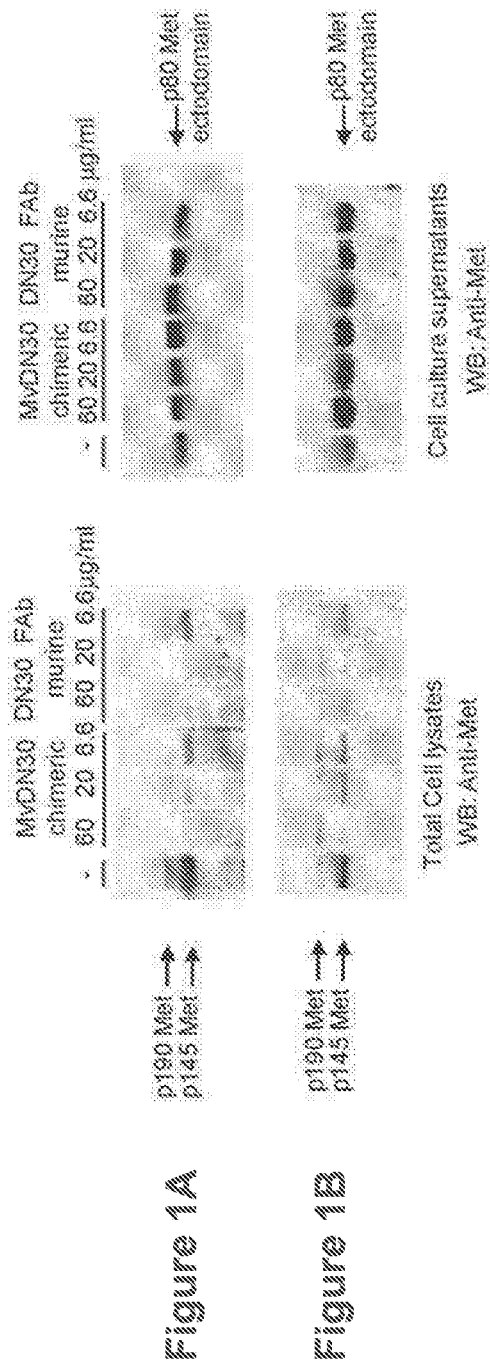
FIGS. 1A-1B: Met shedding and down-regulation in Met-addicted cells treated by chimeric MvDN30 or murine DN30 Fab.

The invention will now be described in detail, by way of non limiting example, with reference to antibody fragments able to specifically bind hepatocyte growth factor receptor.

It is clear that the scope of this description is in no way limited to such target antigen, since the antibody fragments described herein can be characterized by specifically binding other target antigens.

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

Antibodies are complex tetramers in which both the heavy and the light chains are composed by multiple Ig domains, each one folding independently. At the very beginning of the antibody era it has been shown that, through enzymatic treatment, an antibody can originate fragments that maintain the original structure and the antigen-binding properties.

Subsequently, by applying protein engineering techniques, a plethora of different engineered antibody fragments have been generated. According to molecular design, each new antibody fragment is characterized by particular features (i.e. increased avidity, multivalency, multispecificity, ADCC-deficient, chimerized, etc.).

However, none of the previous studies have addressed the issue of renal clearance to prolong half-life in vivo of antibody fragments.

To this end, the present inventors developed a recombinant antibody fragment comprising a first polypeptide comprising a light chain variable domain and two constant domains and a second polypeptide comprising a heavy chain variable domain and two constant domains, wherein two chain constant domains are light chain constant domains and two constant domains are heavy chain CH1 constant domains, fused in different combinations to the variable domains.

In one embodiment, the antibody fragment herein disclosed is more stable in vivo than the Fab molecule comprising said light and heavy chain variable domains.

In one embodiment, the antibody fragment has prolonged half-life in vivo when administered to a human patient than the Fab molecule comprising said light and heavy chain variable domains because of a reduced renal clearance.

These antibody fragments were named 'Dual Constant Domain Fabs' (DCD-Fabs).

In a preferred embodiment, the present disclosure concerns an antibody fragment comprising a first polypeptide comprising a light chain variable domain and two constant domains and a second polypeptide comprising a heavy chain variable domain and two constant domains, wherein two constant domains are human light chain constant domains and two constant domains are human heavy chain CH1 constant domains, fused in different combinations to the variable domains, wherein the antibody fragment is more stable in vivo than the Fab molecule comprising said light and heavy chain variable domains, and wherein the antibody fragment specifically binds the hepatocyte growth factor receptor (HGFR/Met).

In one embodiment, the light chain variable domain is fused at its C-terminus to one light chain constant domain, that is fused at its C-terminus to one light chain constant domain.

In another embodiment, the light chain variable domain is fused at its C-terminus to a light chain constant domain, that is fused at its C-terminus to one heavy chain CH1 constant domain.

In one embodiment, the heavy chain variable domain is fused at its C-terminus to one heavy chain CH1 constant domain, that is fused at its C-terminus to one heavy chain CH1 constant domain.

In another embodiment, the heavy chain variable domain is fused at its C-terminus to a heavy chain CH1 constant domain, that is fused at its C-terminus to a light chain constant domain.

In one embodiment, the constant domains contained in the first and second polypeptide—when coupled together in the antibody fragment—are able to generate disulfide bridges.

In a further preferred embodiment, the present disclosure concerns antibody fragments as defined above wherein the antigen specificity is provided by employing as light and heavy chain variable domains the DN30 light and heavy chain variable domains or humanized light and heavy chain variable domains comprising the complementarity determining regions (CDRs) from DN30 monoclonal antibody. DN30 monoclonal antibody was disclosed in the international patent application WO-A-2007/090807.

An antibody fragment of the invention is generally a therapeutic antibody. For example, an antibody of the invention may be an antagonistic antibody, a blocking antibody or a neutralizing antibody.

In one aspect, the invention provides methods of treating or delaying progression of a disease administering to a subject having the disease an effective amount of an antibody fragment of the invention, effective in treating or delaying progression of the disease.

In one embodiment, the disease is a tumor or tumor metastasis.

In another embodiment, the disease is associated with dysregulation of hepatocyte growth factor-receptor signalling and/or activation.

An antibody fragment of the invention is suitable for treating or preventing pathological conditions associated with abnormalities within the HGF/HGFR signalling pathway.

In one embodiment, an antibody of the invention is a HGFR antagonist.

In one embodiment, the antibody fragment comprises antigen binding sequences from a non-human donor grafted to a heterologous non-human, human or humanized sequence (e.g. framework and/or constant domain sequences). In one embodiment, the non-human donor is a mouse.

In one embodiment, the antigen binding sequences comprise all the CDRs and/or variable domain sequences of an anti-HGFR murine antibody.

In one preferred embodiment, the murine light chain variable domain is fused at its C-terminus to one human kappa light chain constant domain, that is fused at its C-terminus to one human kappa light chain constant domain. In another embodiment, the murine light chain variable domain is fused at its C-terminus to a human kappa light chain constant domain, that is fused at its C-terminus to one human IgG1 heavy chain CH1 constant domain. In one embodiment, the murine heavy chain variable domain is fused at its C-terminus to one human IgG1 heavy chain CH1 constant domain, that is fused at its C-terminus to one human IgG1 heavy chain CH1 constant domain. In another embodiment, the murine heavy chain variable domain is fused at its C-terminus to a human IgG1 heavy chain CH1 constant domain, that is fused at its C-terminus to a human kappa light chain constant domain.

In one preferred embodiment, an antibody fragment of the invention comprises a first polypeptide comprising a light chain variable domain comprising the CDR sequences of an anti-HGFR murine antibody, more preferably the CDRs of DN30, and two constant domains, wherein the two constant domains are: two light chain constant domains or one light chain constant domain and one heavy chain CH1 constant domain. In one embodiment the two constant domains are human constant domains.

In one embodiment, an antibody fragment of the invention comprises a second polypeptide comprising a heavy chain variable domain comprising the CDR sequences of an anti-HGFR murine antibody, more preferably the CDRs of DN30, and two constant domains, wherein the two constant domains are: two heavy chain CH1 constant domains or one heavy chain CH1 constant domain and one light chain constant domain. In one embodiment the two constant domains are human constant domains.

The invention provides, in a most preferred embodiment, a humanized antibody fragment that binds human HGFR, wherein the antibody is effective to inhibit HGF/HGFR activity in vivo, the antibody comprising i) in the heavy chain variable domain (VH) the three CDRs sequence of the heavy chain variable domain of the DN30 monoclonal antibody (SEQ ID Nos.:19,21,23) and substantially a human consensus sequence e.g. substantially the human consensus framework (FR) residues of human heavy chain subgroup and ii) in the light chain variable domain (VL) the three CDRs sequence of the light chain variable domain of the DN30 monoclonal antibody (SEQ ID Nos.:25,27,29) and substantially the human consensus framework (FR) residues of human light chain K subgroup I (VKI).

In one embodiment, an antibody fragment of the invention comprises a first polypeptide comprising as the light chain variable domain the light chain variable domain sequence set forth in SEQ ID NO: 12 (DN30 light chain variable domain) and a second polypeptide comprising as heavy chain variable domain the heavy chain variable domain sequence set forth in SEQ ID NO: 4 (DN30 heavy chain variable domain).

In one aspect, the invention provides for use of an antibody fragment of the invention (e.g. a HGFR antagonist antibody fragment of the invention) in the preparation of a medicament for the therapeutic and/or prophylactic treatment of a disease, such as a cancer, a tumor, a cell proliferative disorder.

In one aspect, the invention provides a method of treating a pathological condition associated with dysregulation of HGFR activation in a subject, said method comprising administering to the subject an effective amount of a HGFR antagonist antibody fragment of the invention, whereby said condition is treated.

In one aspect, the invention provides a method of inhibiting the growth of a cell that expresses HGFR, said method comprising contacting said cell with a HGFR antagonist antibody fragment of the invention thereby causing an inhibition of growth of said cell.

In one aspect, the invention provides a method of therapeutically treating a mammal having a cancerous tumor comprising a cell that expresses HGFR, said method comprising administering to said mammal an effective amount of a HGFR antagonist antibody fragment of the invention, thereby effectively treating said mammal.

In one aspect, the invention provides a method for treating or preventing a cell proliferative disorder associated with increased expression or activity of HGFR, said method comprising administering to a subject in need of such treatment an effective amount of a HGFR antagonist antibody fragment of the invention, thereby effectively treating or preventing said cell proliferative disorder.

In one aspect, the invention provides a method of therapeutically treating a tumor in a mammal, wherein the growth of said tumor is at least in part dependent upon a growth potentiating effect of HGFR, said method comprising contacting a tumor cell with an effective amount of a HGFR antagonist antibody fragment of the invention, thereby effectively treating said tumor. The tumor cell can be one selected from breast, colorectal, lung, colon, pancreatic, prostate, ovarian, cervical, central nervous system, renal, hepatocellular, bladder, gastric, head and neck tumor cell, papillary carcinoma (e.g. the thyroid gland), melanoma, lymphoma, myeloma, glioma/glioblastoma (e.g. anaplastic astrocytoma, glioblastoma multiforme, anaplastic oligodendroglioma, anaplastic oligodendroastrocytoma), leukemia cell. In one embodiment, a cell that is targeted in a method of the invention is a hyperproliferative and/or hyperplastic cell. In one embodiment, a cell that is targeted in a method of the invention is a dysplastic cell. In yet another embodiment, a cell that is targeted in a method of the invention is a metastatic cell. In a further embodiment, a cell that is targeted in a method of the invention is a HGFR expressing cell belonging to the microenvironment sustaining the tumor and/or the metastasis.

Methods of the invention can further comprise additional treatment steps. For example, in one embodiment, a method further comprises a step wherein a targeted tumor cell and/or tissue is exposed to radiation treatment or a chemotherapeutic agent. In another embodiment, a targeted tumor cell and/or tissue is treated, in addition to the antagonist antibody fragment of the invention, with HGF inhibitors (i.e. anti-HGF antibodies) or other anti-HGFR compounds (i.e. small molecule kinase inhibitors). In a further embodiment, a targeted tumor cell and/or tissue is treated, in addition to the antagonist antibody fragment of the invention, with molecules specifically hitting other targets relevant in the maintenance of the transformed phenotype (i.e. anti-EGFR molecules).

Activation of HGFR is an important biological process; its deregulation leads to numerous pathological conditions. Accordingly, in one embodiment of methods of the invention, a cell that is targeted (e.g. a cancer cell) is one in which activation of HGFR is enhanced as compared to a normal cell of the same tissue origin. In one embodiment, a method of the invention causes the death or cell growth arrest of a targeted cell. For example, contact with an antagonist antibody fragment of the invention may result in a cell's inability to signal through the HGFR pathway, which results in cell death or cell growth arrest.

The invention also pertains to immunoconjugates, or antibody-drug conjugates (ADC), comprising an antibody fragment conjugated to a cytotoxic agent such as a chemotherapeutic agent, a drug, a growth inhibitory agent, a toxin (e.g. an enzymatically active toxin of bacterial, fungal, plant, or animal origin, or fragments thereof), or a radioactive isotope (i.e. a radioconjugate).

The use of antibody-drug conjugates for the local delivery of cytotoxic or cytostatic agents, i.e. drugs to kill or inhibit tumor cells growth in the treatment of cancer, allows targeted delivery of the drug moiety to tumors, and intracellular accumulation therein, where systemic administration of these unconjugated drug agents may result in unacceptable levels of toxicity to normal cells as well as the tumor cells sought to be eliminated.

Therapeutic formulations comprising an antibody fragment of the invention are prepared for storage by mixing the antibody fragment having the desired degree of purity with physiologically acceptable carriers, excipients or stabilizers (Remington's Pharmaceutical Sciences 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers; antioxidants; preservatives; low molecular weight (less than about 10 residues) polypeptides; proteins, such as serum albumin, gelatin, or immunoglobulins; hydrophilic polymers such as polyvinylpyrrolidone; amino acids; monosaccharides, disaccharides, and other carbohydrates; chelating agents; sugars; salt-forming counter-ions; metal complexes and/or non-ionic surfactants.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared by means of techniques disclosed i.a. in Remington's Pharmaceutical Sciences 16th edition, Osol, A. Ed. (1980).

The formulations to be used for in vivo administration must be sterile.

Sustained-release preparations may be prepared. Suitable examples of sustained-release preparations include semipermeable matrices of solid hydrophobic polymers containing the antibody fragment of the invention, which matrices are in the form of shaped articles, e.g. films, or microcapsule.

An antibody fragment of the present invention may be used in in vitro, ex vivo and in vivo therapeutic methods. The invention provides various methods based on using antibody fragments having superior properties compared to conventional monovalent antibodies.

The present invention provides antibody fragments, which can be used for a variety of purposes, for example as therapeutics, prophylactics and diagnostics.

Antibody fragments of the invention can be used either alone or in combination with other compositions in a therapy. For instance, an antibody fragment of the invention may be co-administered with another antibody, chemotherapeutic agent(s) (including cocktails of chemotherapeutic agents), other cytotoxic agent(s), anti-angiogenic agent(s), cytokines, and/or growth inhibitory agent(s). Such combined therapies noted above include combined administration (where the two or more agents are included in the same or separate formulations), and separate administration, in which case, administration of the antibody of the invention can occur prior to, and/or following, administration of the adjunct therapy or therapies.

The antibody fragment of the invention (and adjunct therapeutic agent) is/are administered by any suitable means, including parenteral, subcutaneous, intraperitoneal, intrapulmonary, and intranasal, and, if desired for local treatment, intralesional administration. The antibody fragment is suitably administered by pulse infusion, particularly with declining doses of the antibody. Dosing can be by any suitable route, e. g. by injections, such as intravenous or subcutaneous injections, depending in part on whether the administration is brief or chronic. The antibody fragment of the invention can be also delivered by gene transfer by mean of viral vectors (i.e. lentiviral vectors), administered locally or systemically.

The antibody fragment of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as used hereinbefore or about from 1 to 99% of the heretofore employed dosages.

For the prevention or treatment of disease, the appropriate dosage of an antibody fragment of the invention (when used alone or in combination with other agents such as chemotherapeutic agents) will depend on the type of disease to be treated, the type of antibody, the severity and course of the disease, whether the antibody fragment is administered for preventive or therapeutic purposes, previous therapy, the patient's clinical history and response to the antibody, and the discretion of the attending physician. The antibody fragment is suitably administered to the patient at one time or over a series of treatments. Depending on the type and severity of the disease, about 1 mg/kg to 15 mg/kg of antibody is an initial candidate dosage for administration to the patient, whether, for example, by one or more separate administrations, or by continuous infusion. One typical daily dosage might range from about 1 mg/kg to 100 mg/kg or more, depending on the factors mentioned above. For repeated administrations over several days or longer, depending on the condition, the treatment is sustained until a desired suppression of disease symptoms occurs. One exemplary dosage of the antibody fragment would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e. g. every week or every three weeks (e. g. such that the patient receives from about two to about twenty, e. g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Results

Generation of the Chimeric DN30 Fab and Characterization of its Biochemical and Biological Properties.

Figure 2A:
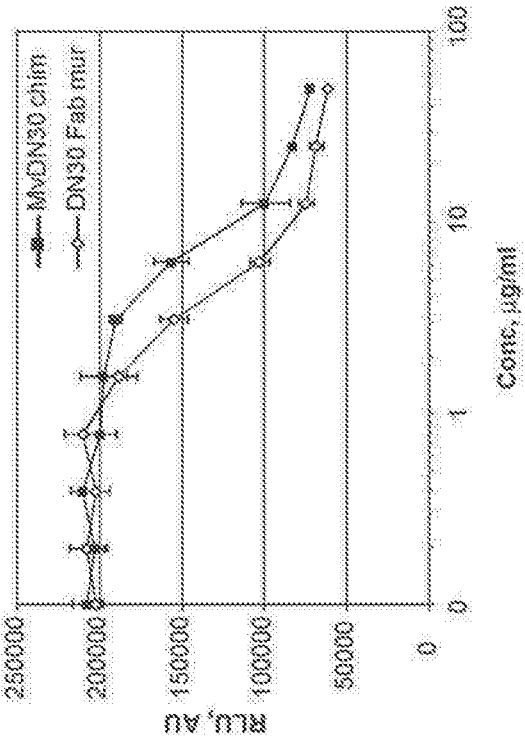
FIGS. 2A-2B: Growth assay of Met-addicted cells treated by chimeric MvDN30 or murine DN30 Fab.
Figure 2B:
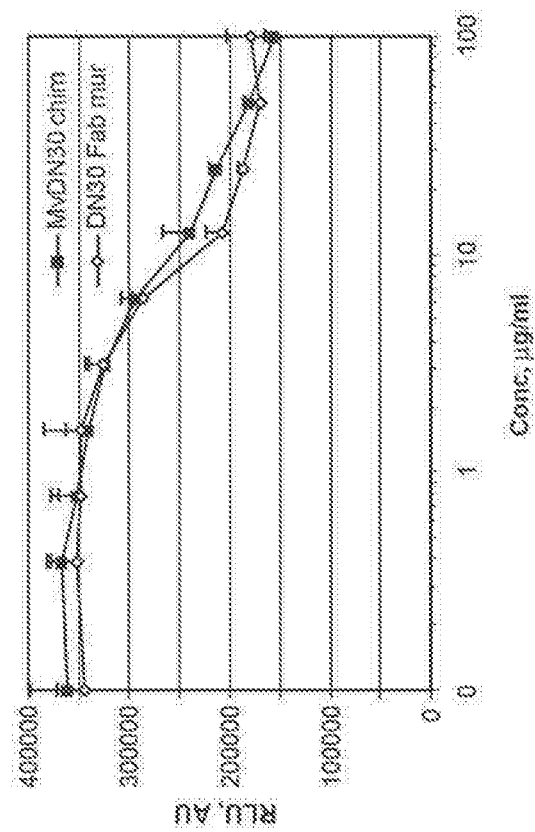

Like other monoclonal antibodies with therapeutic potential, DN30 has been raised in mice. Thus, its direct employment in humans for therapeutic purpose is not applicable, as the murine molecule would be recognized by human anti-murine antibodies (HAMA) that leads to immuno-mediated clearance of the antibody activity. Substitution of the murine constant regions of the antibody with sequences derived from human immunoglobulins (antibody chimerization) is sufficient to strongly reduce the HAMA response. Chimerized mAbs and Fabs are currently used in the clinic. Through classical molecular biology techniques, the present inventors have substituted the constant domains of the DN30 Fab heavy and light chains with constant domains derived from human immunoglobulins: the light chain constant domain has been substituted with the human kappa type domain, the one more represented in the natural human antibodies, while the heavy chain CH1 constant domain has been substituted with the homologous domain derived from the human IgG1. This combination is effective: the chimerized DN30 Fab (MvDN30) binds Met with high affinity, induce Met shedding and inhibits proliferation of Met-addicted cells, overlapping the properties of the corresponding murine molecule (FIG. 1 and FIG. 2).

Molecular Design of the Dual Constant Domain Fab.

Figure 3:
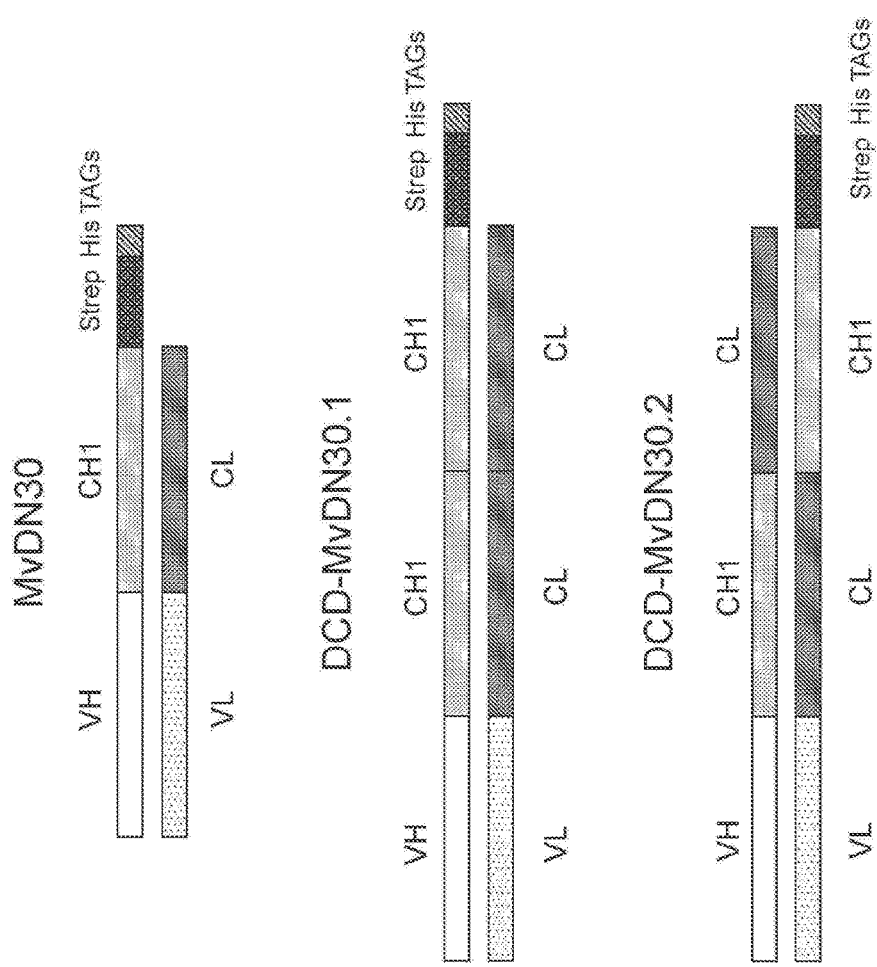
FIG. 3: Schematic representation of the new DN30 derived molecules. Top: chimerized DN30 Fab (MvDN30); middle: Double Constant Domain Fab with the duplicated constant domains in tandem (DCD-MvDN30.1); bottom: Double Constant Domain Fab with the duplicated constant domains swapped reciprocally (DCD-MvDN30.2). VH: variable domain of the DN30 heavy chain. VL: variable domain of the DN30 light chain. CH1: constant domain 1 derived from human IgG1 heavy chain. CL: constant domain derived from human kappa light chain. Strep and His Tag: sequences included to allow protein purification and immuno-detection.
Figure 4:
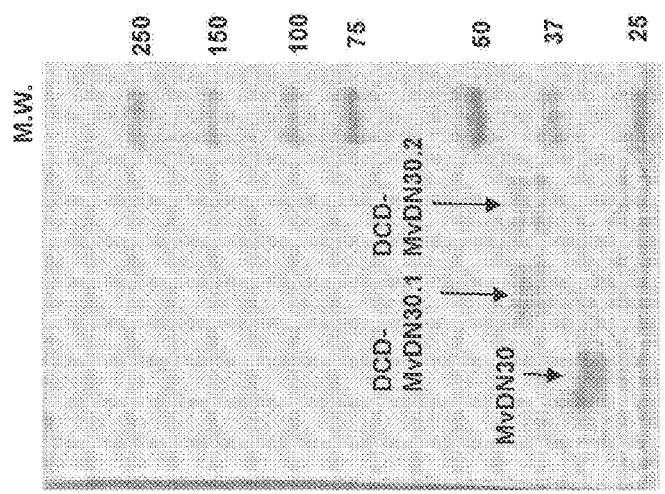
FIG. 4: Analysis of the new DN-30 derived molecules. The indicated purified proteins were subjected to SDS-PAGE under reducing condition. Gel was stained with Gel Code blue (Pierce). All the molecules show two bands with the expected molecular weight.

Using the MvDN30 sequence as a template, the present inventors duplicated the constant domains in each light and heavy chain (Dual Constant Domain-Fab). The new engineered molecule has a predicted molecular weight of 75 kD. The present inventors generated two different DCD-Fabs. In the first molecule the human constant domains were duplicated in tandem, thus generating a VH-CH1-CH1 chimeric heavy chain and a VL-CL-CL chimeric light chain. In the second molecule the terminal domain were swapped reciprocally, thus generating a VH-CH1-CL chimeric heavy chain and a VL-CL-CH1 chimeric light chain (FIG. 3). The corresponding dimeric recombinant molecules were named DCD-MvDN30.1 and DCD-MvDN30.2. cDNAs encoding for these new molecules were cloned into an expression plasmid and then expressed into eukaryotic cells. Protein were purified from cell culture supernatant thank to the StrepTAG that was inserted at the C-terminus of the sequence. FIG. 4 shows the SDS-Page separation under reducing condition of the purified recombinant molecules having the correct molecular weight size.

DCD-MvDN30.1 and DCD-MvDN30.2 Bind to Met with High Affinity.

Figure 5:
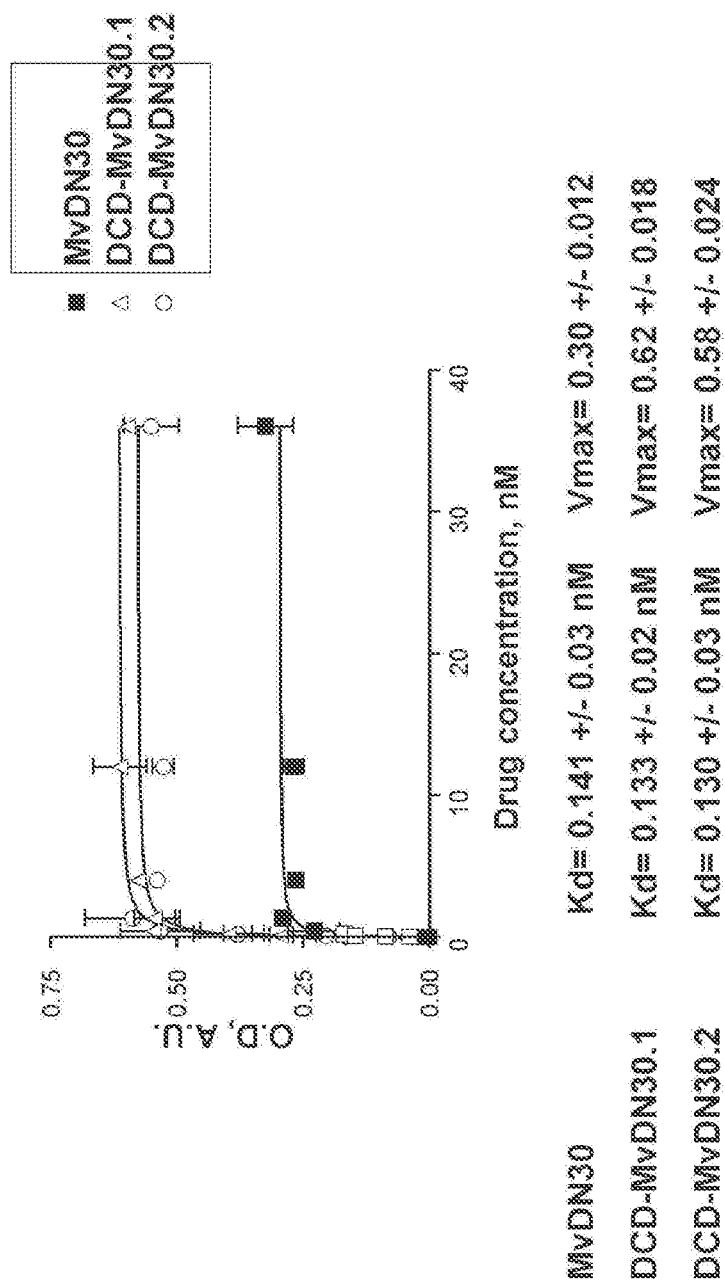
FIG. 5: Binding to Met of DCD-MvDN30 molecules. ELISA binding analysis of MvDN30, DCD-MvDN30.1 and DCD-MvDN30.2 (liquid phase) to a Met-Fc chimera (solid phase). Binding was revealed using anti-strepTAG antibodies. O.D.: Optical Density; A.U.: arbitrary units. Each point is the mean of triplicate values; bars represent standard deviation. The new molecules bind to Fc-Met with the same high affinity.

Purified DCD-MvDN30.1 and DCD-MvDN30.2 were characterized for their ability to bind the Met receptor. To this end, the present inventors performed ELISA assays using Met ectodomain in solid phase and MvDN30, DCD-MvDN30.1 and DCD-MvDN30.2 in liquid phase. Binding was revealed using anti-strepTAG antibodies (FIG. 5). This analysis showed that the three DN30-derived monovalent molecules bind to Met with a similar affinity (MvDN30, $K_d$=0.141±0.03 nM; DCD-MvDN30.1, $K_d$=0.133±0.02 nM; DCD-MvDN30.2, $K_d$=0.130±0.03 nM).

DCD-MvDN30.1 and DCD-MvDN30.2 do not Induce Met Phosphorylation.

Figure 6:
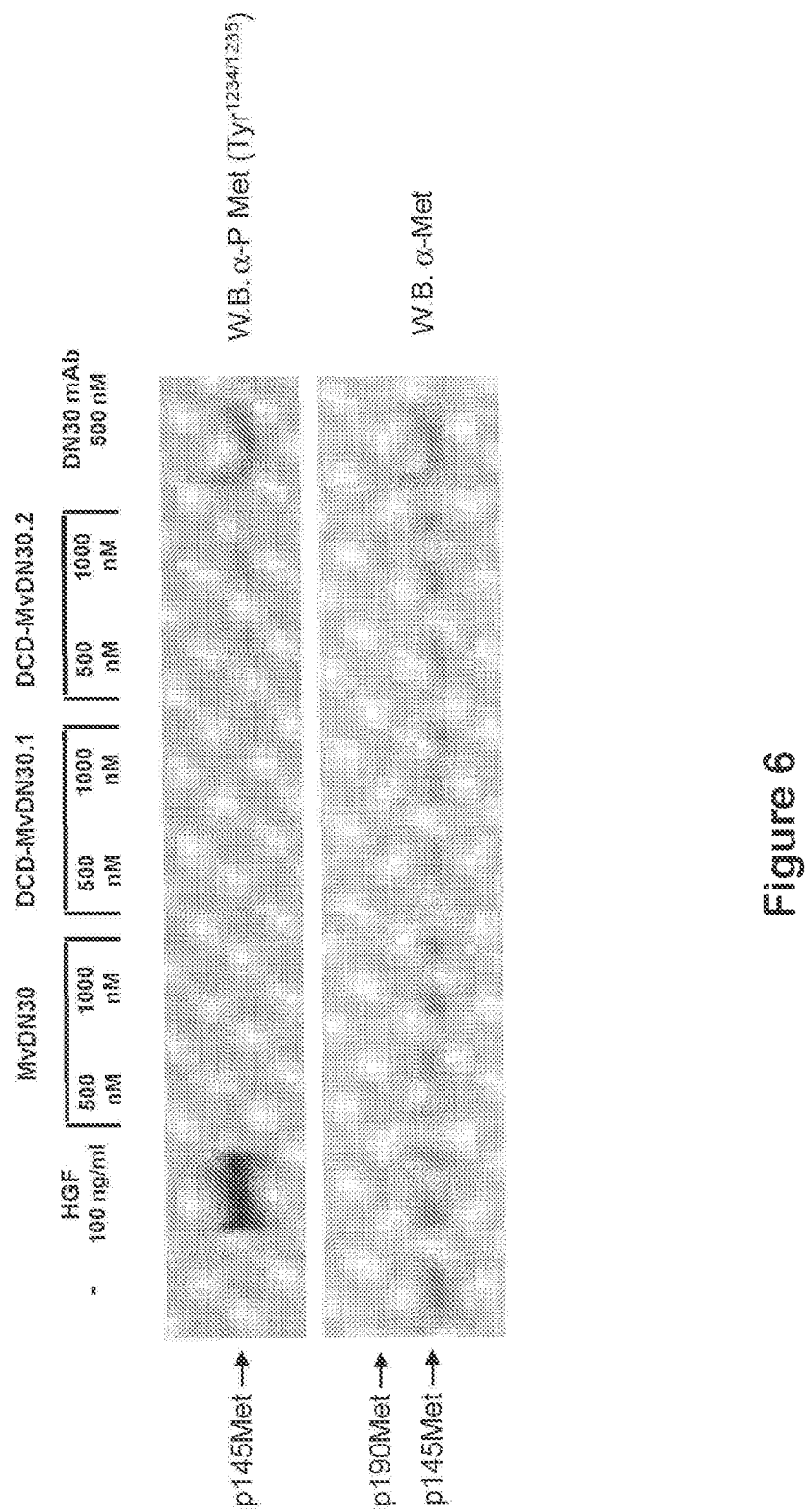
FIG. 6: Agonistic activity of DCD-MvDN30 molecules. A549 cells were starved for 24 hrs and then stimulated for 10 min at 37° C. with the different molecules at the indicated concentrations. Met activation was determined by immuno-precipitation with anti-Met antibodies followed by Western blotting with anti-Met antibodies specific for the phosphorylated Tyr 1234/1235 Met residues, the major phosphorylation site (Top). The same blot was re-probed with anti-Met antibodies (Bottom). The new molecules do not significantly activate the Met receptor.
Figure 7:
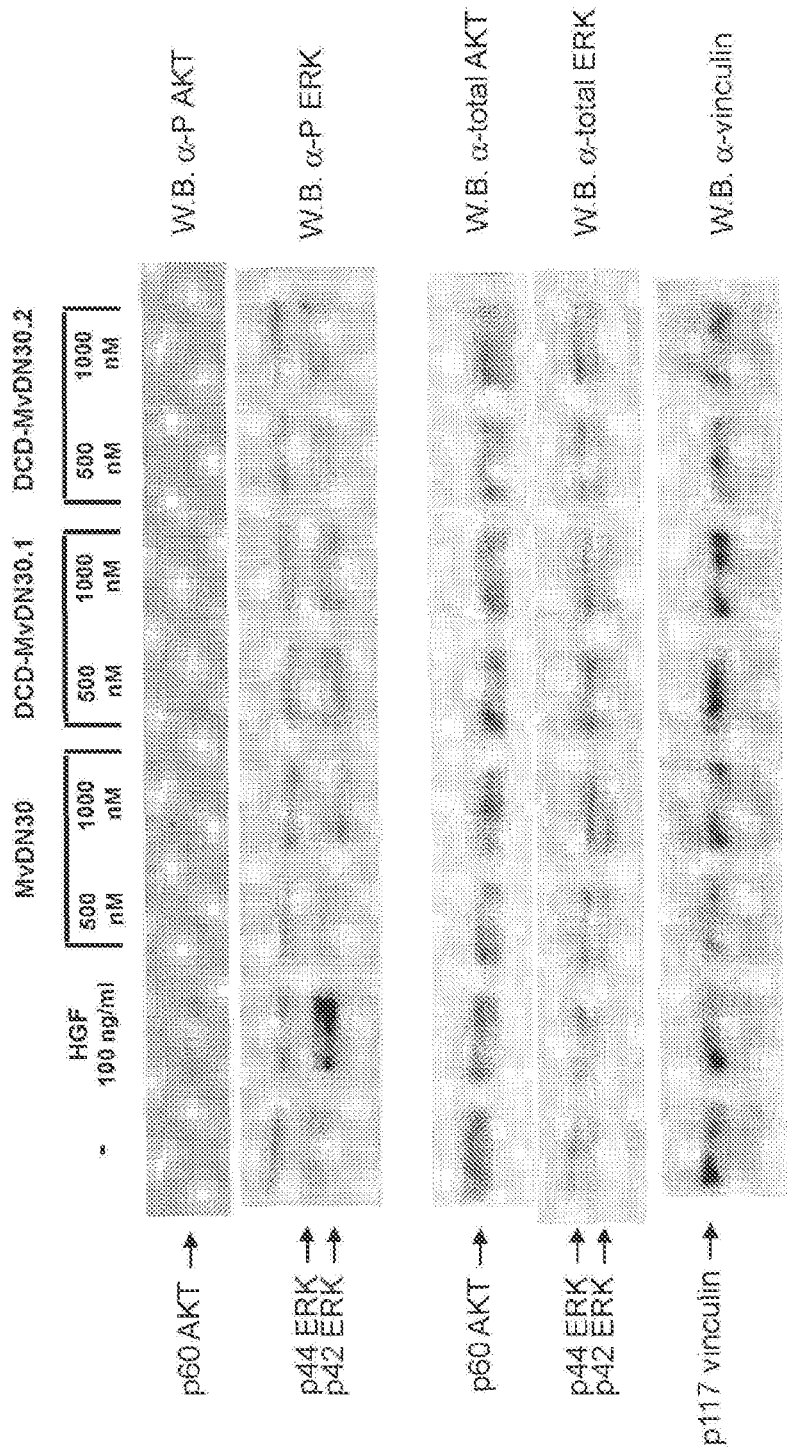
FIG. 7: Agonistic activity of DCD-MvDN30 molecules. A549 cells were starved for 24 hrs and then stimulated for 10 min at 37° C. with the different molecules at the indicated concentrations. Activation of AKT and ERK-1,2 was determined by Western blotting with anti-AKT or anti-ERK antibodies specific for the phosphorylated form. The same blot was re-probed with anti-Vinculin antibodies (Bottom) to control protein loading. The new molecules do not significantly activate the Met-dependent signaling.

The present inventors tested whether the new DN30-derived molecules could display a Met agonistic activity in Met phosphorylation assay. This was analysed using A459 human lung carcinoma cells, which represent a standard system for determining Met activation in response to acute ligand stimulation. In fact, A549 cells express physiological levels of Met, inactive in basal conditions, but prone to be activated by HGF or a ligand-mimetic molecule (4, 10). Cells were stimulated for 15 minutes with increasing amounts of MvDN30, DCD-MvDN30.1 and DCD-MvDN30.2. Cells were also stimulated with HGF and DN-30 mAb as positive controls. Met activation was determined by immunoblotting with anti-phosphoMet antibodies. As shown in FIG. 6, the new molecules did not show any significant agonistic activity. DCD-MvDN30.1 was indistinguishable from MvDN30, being devoid of any agonistic activity. DCD-MvDN30.2 retained a minimal residual agonist activity, which was in any case negligible compared with the DN30 mAb or HGF. The present inventors also checked the activation of molecules acting as downstream effectors of Met. While stimulation with HGF induced the activation of both Extracellular signal-Regulated Kinases 1 and 2 (ERK-1 and ERK-2) and AKT/Protein Kinase B (AKT), DCD-MvDN30.1 and DCD-MvDN30.2, as MvDN30, did not affect the phosphorylation status of these signal transducers (FIG. 7).

DCD-MvDN30.1 and DCD-MvDN30.2 Induce Met Shedding.

Figure 8:
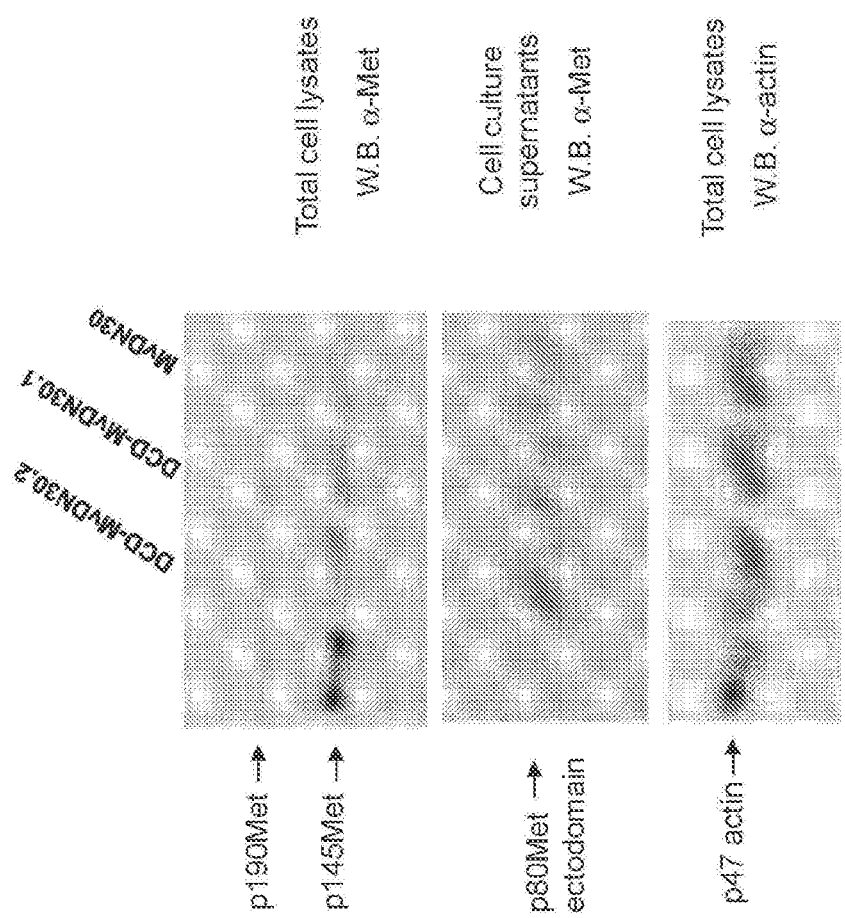
FIG. 8: Met shedding and down-regulation in cells treated by DCD-MvDN30 molecules. A549 cells were incubated for 72 hrs in serum free medium with the indicated molecules (500 nM). Total Met levels were determined by Western blot analysis of cell extracts using anti-Met antibodies. The two Met bands correspond to the unprocessed (p190 Met) and mature (p145 Met) forms of the receptor. As a loading control, the filter was probed with an unrelated protein (actin). Met shedding was determined by Western blot analysis of conditioned medium using anti-Met antibodies. The new molecules efficiently induce Met shedding.

The present inventors also investigated whether the new molecules derived from MvDN30 maintain the ability to promote receptor shedding and downregulation. A549 cells were incubated with DCD-MvDN30.1, DCD-MvDN30.2 and MvDN30. After 48 hours, the presence of Met ectodomain in the conditioned medium was analyzed by immunoblotting using a monoclonal antibody directed against the extracellular portion of Met. Total cellular levels of Met were also determined on cell lysates using the same antibody. This analysis revealed that both DCD-MvDN30.1 and DCD-MvDN30.2 efficiently induced Met shedding and promoted Met down-regulation, resulting in release of soluble Met ectodomain in the extracellular space and decreased Met levels in the cell (FIG. 8). Therefore, the new MvDN30 derived molecules, like MvDN30, achieved complete disassociation between the antagonistic and agonistic properties of the parental DN-30 mAb.

DCD-MvDN30.1 and DCD-MvDN30.2 Inhibit HGF-induced Met Phosphorylation and Down-stream Signaling.

Figure 9:
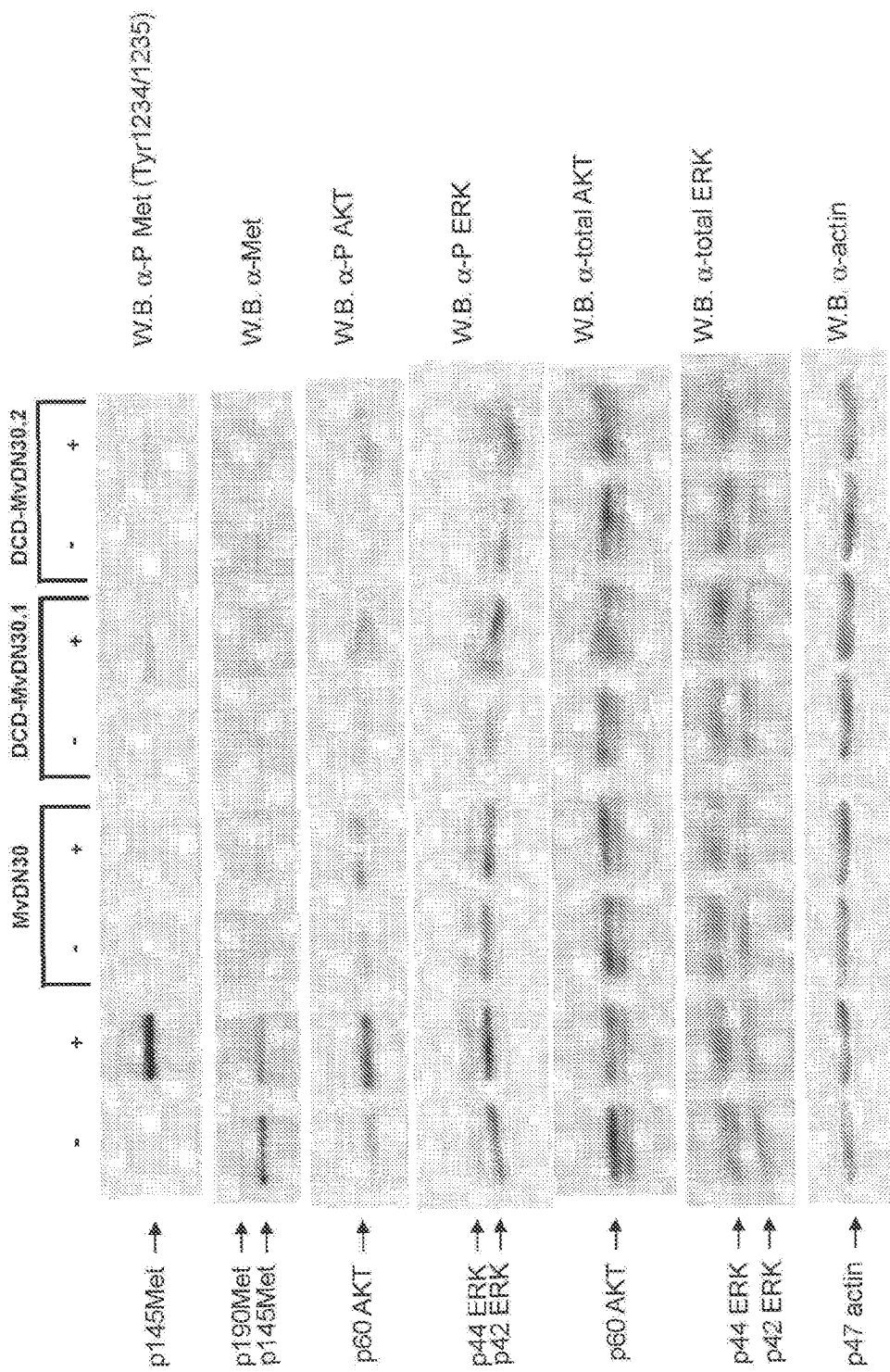
FIG. 9: Inhibition of HGF-induced Met-activation by DCD-MvDN30 molecules. A549 cells were incubated for 24 hrs in serum free medium plus the indicated molecules (1000 nM) and then stimulated for 10 min with HGF (100 ng/ml). Met activation was determined in total cell lysates by Western blotting with anti-Met antibodies specific for the phosphorylated Tyr 1234/1235 Met residues, the major phosphorylation site. The same blot was re-probed with anti-Met antibodies. Activation of AKT and ERK-1,2 was determined by Western blotting with anti-phosphoAKT or anti-phosphoERK antibodies. The same blot was re-probed with anti-AKT or ERK-1,2 antibodies. To control protein loading the filter was also probed with anti-Vinculin antibodies. The new molecules strongly inhibit HGF-induced Met-activation and Met-dependent signaling.
Figure 10A:
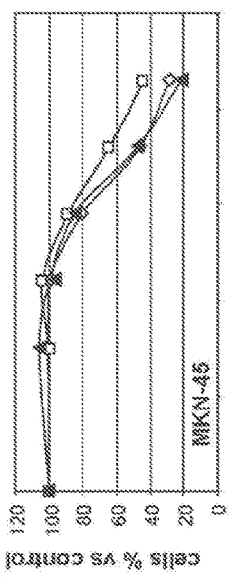
FIGS. 10A-10F: Anchorage-dependent growth of Met-addicted cells treated with DCD-MvDN30.1 or DCDM-vDN30.2 or MvDN30.
Figure 10B:
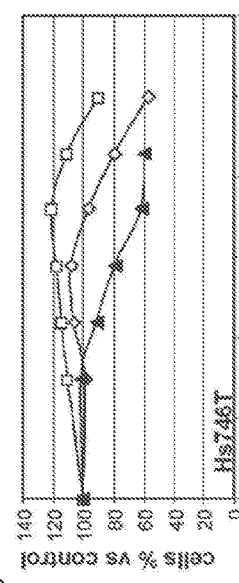
Figure 10D:
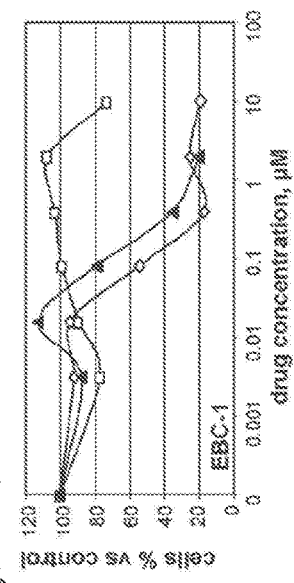
Figure 10C:
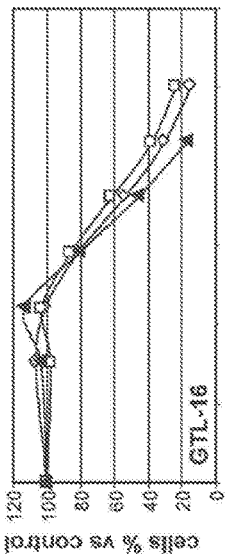
Figure 10E:
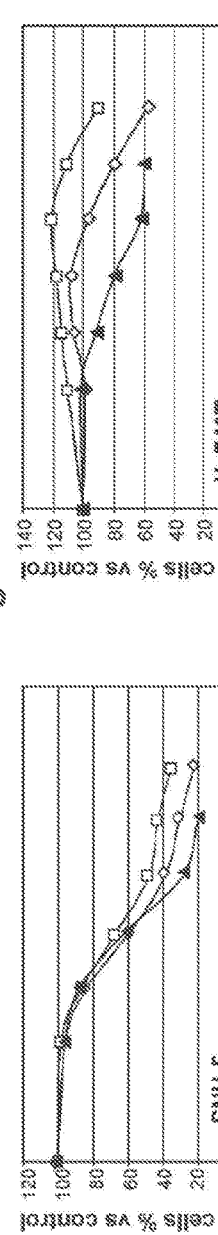
Figure 10F:
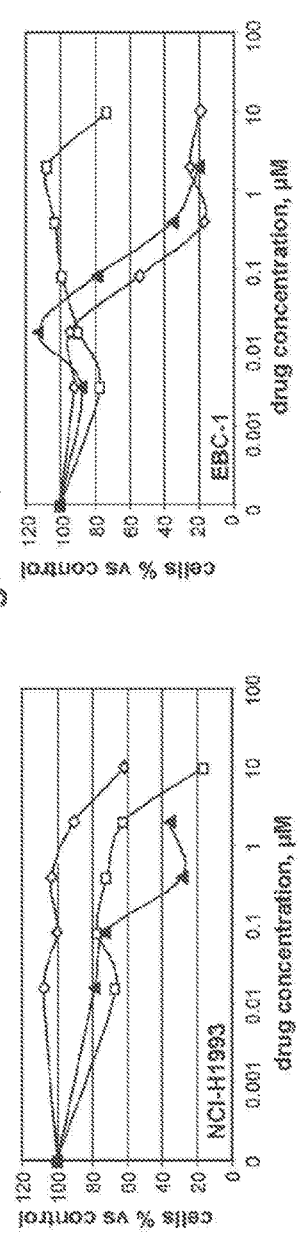

The present inventors investigated if DCD-MvDN30.1 and DCD-MvDN30.2 could inhibit HGF-induced Met phosphorylation and down-stream signaling. A549 cells were incubated with DCD-MvDN30.1, DCD-MvDN30.2 and MvDN30 for 24 hrs and then stimulated for 15 minutes with HGF. Met activation was determined by immunoblotting with anti-phosphoMet antibodies. As shown in FIG. 9, the two engineered molecules, as MvDN30, efficiently downregulated Met receptor and strongly impaired the level of its phosphorylation. This resulted in an inhibition of AKT and ERK-1,2 activation (FIG. 9).

DCD-MvDN30.1 and DCD-MvDN30.2 Inhibit MET-addicted Anchorage-dependent Cell Growth.

Anchorage-dependent growth can be impaired by a Met-inhibitor only in the cells that rely on Met-signalling for proliferation/survival, the so called MET-addicted cells. The present inventors analysed the complete panel of MET-addicted tumor cells (GTL-16, SNU-5, Hs746T, MKN-45—human gastric carcinoma cells—and H1993, EBC-1—human lung carcinoma cells). Exponentially growing cells were incubated with increasing concentrations of DCD-MvDN30.1 and DCD-MvDN30.2. MvDN30 was included in the assay as positive control. After 72 hours cell growth was determined using a luminescence-based ATP assay. Both the MvDN30-derived molecules inhibited all the MET-addicted cell growth in a dose-dependent fashion (FIG. 10). Inhibitory properties of the two DCD molecules were comparable to the ones of MvDN30 in all cells tested.

DCD-MvDN30.1 and DCD-MvDN30.2 Inhibit Anchorage-independent Cell Growth.

Figure 11:
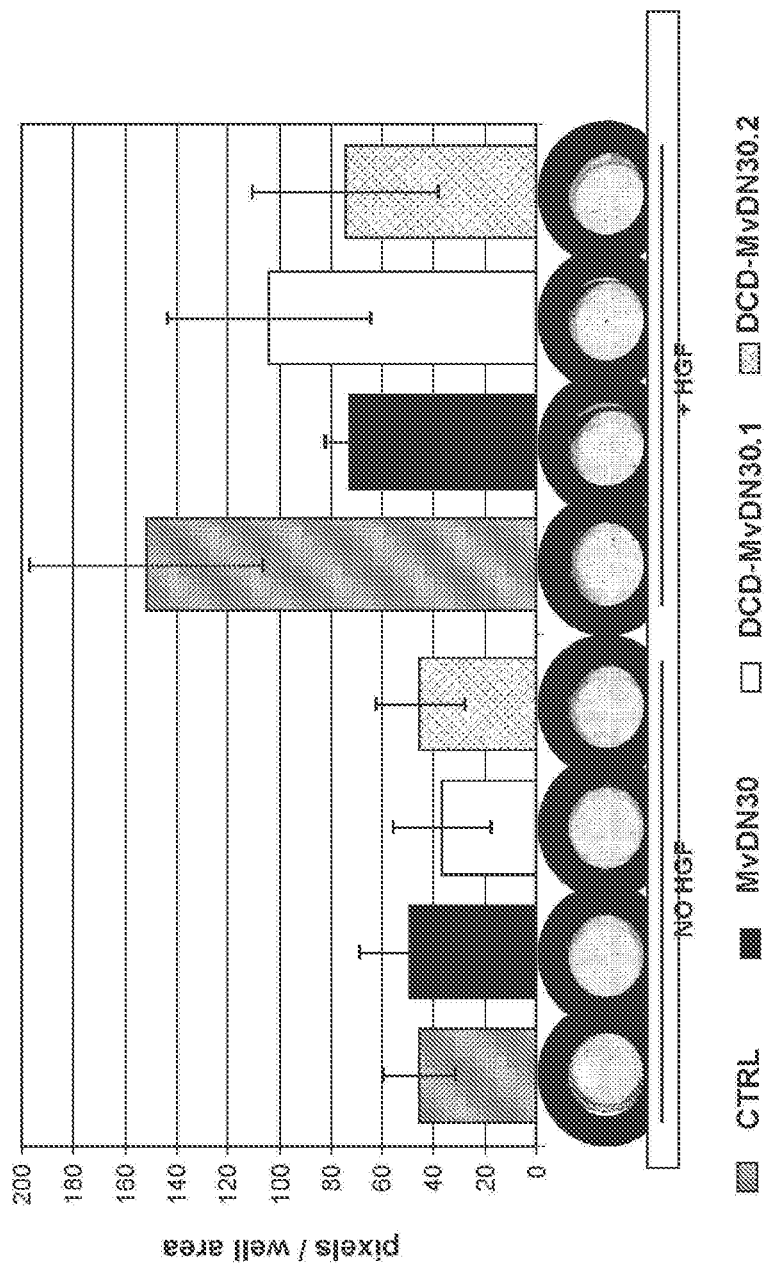
FIG. 11: Anchorage-independent growth of cells treated with DCD-MvDN30.1 or DCD-MvDN30.2 or MvDN30. A549 cells were plated in semi-solid medium (5% agarose) with or without HGF (50 ng/ml) in the presence of 1.5 mM of DCD-MvDN30.1, or DCD-MvDN30.2 or MvDN30. After 21 days colonies were stained with tetrazolium salt. Colonies were quantified by counting pixel in each well area with MetaMorphOffline Software. Each point is the mean of triplicate values. The new molecules efficiently inhibit HGF-dependent anchorage-independent cell growth.

The present inventors tested the ability of DCD-MvDN30.1 and DCD-MvDN30.2 to inhibit anchorage independent growth of A549 cells. Cells were seeded in semisolid medium incubated or not with HGF and treated with a single dose of DCD-MvDN30.1, DCD-MvDN30.2 and MvDN30. After two weeks, cell colonies were stained and quantified. In this assay as well, DCD-MvDN30.1 and DCD-MvDN30.2 reduced HGF-dependent colony formation in a fashion similar to that of MvDN30 (FIG. 11).

DCD-MvDN30.1 and DCD-MvDN30.2 Show Improved Pharmacokinetic Profile In Vivo Compared to MvDN30.

Figure 12:
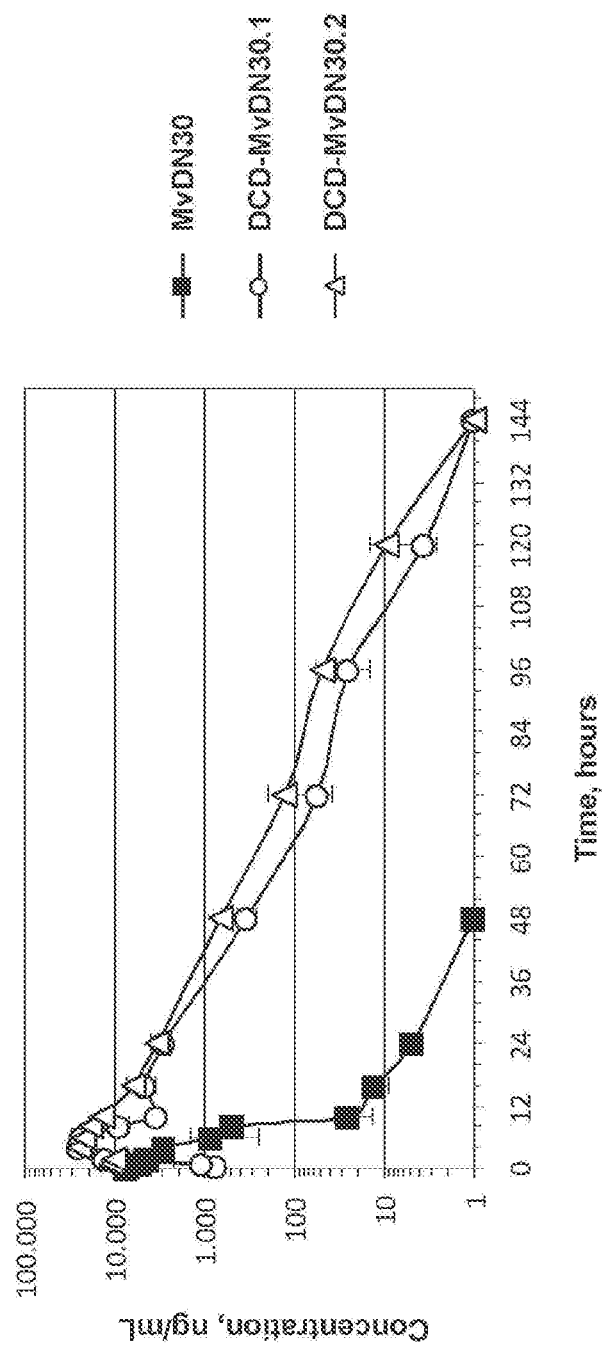
FIG. 12: Pharmacokinetic profile in vivo of DCD-MvDN30.1, DCD-MvDN30.2 and MvDN30. Immunodeficient mice were injected intraperitoneous with a single dose (100 µg) of DCD-MvDN30.1, or DCD-MvDN30.2 or MvDN30. Peripheral blood was collected at different time points. Serum concentrations of the therapeutic molecules were measured by ELISA. Graph represents the amount of circulating molecules in function of time. Samples are in triplicate, bars represent standard deviations.

The present inventors studied the pharmacokinetic properties of DCD-MvDN30.1 and DCD-MvDN30.2, in comparison with MvDN30. A single dose of the above mentioned molecules were delivered by intraperitoneal injection to immunodeficient mice. Peripheral blood from the treated mice was collected at different time points after the delivery. The circulating concentrations of the studied molecules were determined by ELISA performed on the serum samples. DCD-MvDN30.1 and DCD-MvDN30.2 reached higher circulating levels compared to MvDN30. Moreover both the molecules showed increased half-life and are longer lasting in the circulation, being biological available for a longer time. DCD-MvDN30.1 and DCD-MvDN30.2 clearance is strongly improved compared to MvDN30 (clearance reduction compared to MVDN30: 9.6 and 13.7 fold respectively for DCD-MvDN30.1 and DCD-MvDN30.2) (FIG. 12 and Table 1).

TABLE 1

Pharmacokinetic parameters of the different DN30-derived molecules

|  | $t^{1/2}$ | CL (ml/h) | Vss (ml) | Cmax (ng/ml) | Tmax (h) | AUCtot (ng/ml)h | kel (1/h) |
|---|---|---|---|---|---|---|---|
| MVDN30 | 8.41 | 4.36 | 11.96 | 7595 | 0.5 | 22933 | 0.082 |
| DCD-MvDN30.1 | 10.53 | 0.45 | 5.77 | 24130 | 4 | 220188 | 0.066 |

TABLE 1-continued

Pharmacokinetic parameters of the different DN30-derived molecules

|  | t½ | CL (ml/h) | Vss (ml) | Cmax (ng/ml) | Tmax (h) | AUCtot (ng/ml)h | kel (1/h) |
|---|---|---|---|---|---|---|---|
| DCD-MvDN30.2 | 10.27 | 0.32 | 4.36 | 24952 | 4 | 314667 | 0.068 | t½: half-life; CL: clereance; Vss: Volume of distribution; Cmax: maximal molecule concentration; Tmax: time to reach Cmax; AUCtot: area under the Curve; Kel: constant of elimination.

Material and Methods

Cell Culture

EBC-1 human lung carcinoma cell and MKN-45 gastric carcinoma cell line were obtained from the Japanese Collection of Research Bioresources (Osaka, Japan). GTL-16 human gastric carcinoma cells were derived from MKN-45 cells as described (11). All other cell lines were obtained from the ATCC-LGC Standards partnership (Sesto San Giovanni, Italy). All cell lines were maintained in RPMI except Hs746T—in DMEM—and SNU-5—in IMDM. Cell media were supplemented with 10% (20% for SNU-5) Fetal Bovine Serum and 2 mM glutamine (Media, serum and glutamine were from Sigma Life Science, St. Louis, Mo.).

Protein Engineering

DCD-MvDN30.1 and DCD-MvDN30.2 are comprised of a heavy chain and a light chain.

The DCD-MvDN30.1 heavy chain (SEQ ID NO.:1 and 2) corresponds to the VH domain of wild-type DN30 Fab (2; SEQ ID No.: 3 and 4) fused to the CH1 domain of human immunoglobulin G1 repeated in tandem (SEQ ID NO.: 5 and 6). At the C-terminus, a STREP tag (ST, SEQ ID NO.:7) and a poly-histidine tag (HT, SEQ ID NO.:8) have been added for purification and detection purposes. The overall structure corresponds to (from the N- to the C-terminus): VH-CH1-CH1-ST-HT. The nucleotide and amino acid sequences of the heavy chain of DCD-MvDN30.1 are reported in FIG. 14A and B, respectively.

The DCD-MvDN30.1 light chain (SEQ ID No.:9 and 10) corresponds to the VL domain of wild-type DN30 Fab (SEQ ID No.:11 and 12) fused to the CL domain of human immunoglobulin kappa (SEQ ID NO.:13 and 14) repeated in tandem. The overall structure corresponds to (from the N- to the C-terminus): VL-CL-CL. The nucleotide and amino acid sequences of the light chain of DCD-MvDN30.1 are reported in FIG. 13A and B, respectively.

The DCD-MvDN30.2 heavy chain (SEQ ID No.:15 and 16) corresponds to the VH domain of wild-type DN30 Fab (SEQ ID No.:3 and 4) fused to the CH1 domain of human immunoglobulin G1 (SEQ ID NO.: 5 and 6) plus the CL region of human immunoglobulin kappa (SEQ ID NO.:13 and 14). The overall structure corresponds to (from the N- to the C-terminus): VH-CH1-CL. The nucleotide and amino acid sequences of the heavy chain of DCD-MvDN30.2 are reported in FIG. 16A and B, respectively.

The DCD-MvDN30.2 light chain (SEQ ID No.:17 and 18) corresponds to the VL domain of wild-type DN30 Fab (SEQ ID No.:11 and 12) fused to the CL domain of human immunoglobulin kappa (SEQ ID NO.:13 and 14) plus the CH1 of human immunoglobulin G1 (SEQ ID NO.: 5 and 6) plus the STREP tag (ST, SEQ ID NO.:7) and the poly-histidine tag (HT, SEQ ID NO.:8). The overall structure corresponds to (from the N- to the C-terminus): VL-CL-CH1-ST-HT. The nucleotide and amino acid sequences of the light chain of DCD-MvDN30.2 reported in FIG. 15A and B, respectively.

The cDNAs encoding DCD-MvDN30.1 and DCD-MvDN30.2 were synthesized chemically by the GeneArt® service (Life Technologies, Paisley, United Kingdom). The nucleotide and amino acid sequences of DN30 Fab light and heavy chain variable domains are reported in FIGS. 17 and 18, respectively. The CDR regions are underlined both in the nucleotide and amino acid sequences, wherein the CDRs of the heavy chain variable domain have the amino acid and nucleotide sequences set forth in SEQ ID Nos.:19,21,23 and 20,22, respectively, and the CDRs of the light chain variable domain have the amino acid and nucleotide sequences set forth in SEQ ID Nos.:25, 27,29 and 26,28,30 respectively.

All constructs were engineered to contain a BamHI site at the 5' end and a NotI site at the 3' end. The BamHI-NotI fragments were subcloned into the pUPEX expression vector (U-Protein Express, Utrecht, The Netherlands). Medium-scale production of DCD-MvDN30.1 and DCD-MvDN30.2 was outsourced to U-Protein Express that achieved it by transient transfections into HEK (Human Epithelial Kidney) cells. Proteins were purified by affinity chromatography using the STREP tag and the poly-histidine tag. Purified proteins were conserved in PBS plus 0.02% Tween-80 (Sigma-Aldrich) and stored at 4° C. Purity was determined by SDS-PAGE in both reducing and non-reducing conditions followed by Coomassie staining.

Immunoprecipitation and Western Blotting

Immunoprecipitation was performed as described (12) using the DO-24 anti-Met mAb (4). Western blotting was performed using the following antibodies: anti-human Met mAb clone DL-21 that recognizes a domain located in the extracellular portion of Met (4); anti-phosphotyrosine mAb clone 4G10 mAb (Millipore, Temecula, Calif.); anti-phospho-Met (Tyr 1234/1235), anti-phospho-Met (Tyr 1349), anti-phospho-Akt (Ser 473), anti-Akt, anti-phospho-ERK (Thr 202/Tyr 204) and anti-ERK polyclonal Abs (Cell Signaling Technology, Beverly, Mass.).

ELISA Binding Assays

Binding of MvDN30, DCD-MvDN30.1 and DCD-MvDN30.2 was determined by ELISA using a Met-Fc chimera in solid phase (R&D Systems, Minneapolis, Minn.) and increasing concentrations of FLAG-tagged recombinant antibody in liquid phase. Binding was revealed using an anti-strepTAG II antibody conjugated with horseradish peroxidase (IBA, Olivette, Mo.). Data were analyzed and fit using Prism software (Graph Pad Software, San Diego, Calif.). Met-Fc chimera is a fusion protein wherein the Fc domain derived from a human IgG is fused in frame with the Met extracellular portion.

Met Activation Analysis

Subconfluent A549 human lung carcinoma cells were incubated in serum-free medium for 48 hours and then stimulated for 10 minutes with the indicated concentrations of recombinant HGF (R&D Systems) or purified DN-30 mAb, MvDN30, DCD-MvDN30.1 and DCD-MvDN30.2 as described (13). Following stimulation, cells were immediately lysed and processed as described (12). Cell extracts were immunoprecipitated with anti-Met antibodies (DO-24), resolved by SDS-PAGE and analyzed by Western blotting using anti-phosphotyrosine antibodies (Millipore). The same blots were re-probed with anti-Met antibodies (DL-21) to normalize the amount of Met immunoprecipitated.

For the inhibition of HGF-induced Met phosphorylation A549 cells were treated for 24 hrs in serum free medium with MvDN30, DCD-MvDN30.1 and DCD-MvDN30.2 and than stimulated with HGF as described above. Cell monolayers were lysated with Laemmli buffer and equal amounts of total proteins, separated into acrylammide gel by SDS-PAGE and analyzed by immunoblotting with anti-phospho-Met (Tyr 1234/1235) antibodies.

Analysis of Met Shedding

Subconfluent A549 monolayers were washed twice with PBS and then incubated in serum-free medium with the indicated concentrations of DN-30 FAb or mAb. After 48 hours, conditioned medium was collected and cells were lysed with Laemmli Buffer. Met protein levels were determined in 50 µg of total cell lysates and in 50 µl of cell culture supernatant by Western blotting using the anti-Met DL-21 mAb.

In Vitro Biological Assays

For cell growth analysis, cells were seeded in 96 well-dishes (1,000 cells/well) in medium containing 10% FBS. After 24 hours, the medium was replaced with fresh one containing the DN30-derived molecules plus 5% FCS antibodies at the indicated concentrations. Cell number was evaluated after 72hrs using the CellTiter-Glo luminescent cell viability assay (Promega Corporation, Madison, Wis.) according to manufacturer's instructions. Chemo-luminescence was detected with a Multilabel Reader PerkinElmer 2030 apparatus (PerkinElmer Life and Analytical Sciences, Turku, Finland).

For anchorage-independent growth assays, cells were seeded in 48 well-dishes (500 cells/well) in medium containing 2% FBS and 0.5% SeaPlaque agarose (BMA, Rockland, Me.). Antibodies (1.5 µM) and HGF (50 ng/ml) were added in the culture medium every 3 days. After 21 days of culture, colonies were stained by tetrazolium salts (Sigma Life Science) and scored by MetaMorphOffline Software (Molecular Device LLC, Sunnyvale, Calif.).

Pharmakokinetic Analysis

Adult immunodeficient NOD-SCID mice (body weight between 18 and 22 gr, on average 20 gr) were injected IP with 100 µg of DCD-MvDN30.1 or DCD-MvDN30.2 or MvDN30. Peripheral blood was collected at different time (for MvDN30: 10, 20 and 30 min, 1, 2, 4, 6, 8, 10, 16, 24, 48 hours; for DCD-MvDN30.1 and DCD-MvDN30.2: 30 min, 1, 2, 4, 6, 8, 10, 16, 24, 48, 72, 96, 144 hrs after the delivery). Therapeutic molecule concentrations were evaluated by ELISA as described above in binding assay section, interpolating the absorbance values of the samples on the linear part of a standard curve obtained by serial dilutions of the different purified molecules. Each time point was the average value of a least 3 mice.

REFERENCES

1) Martens, T., et al. A novel one-armed anti-c-Met antibody inhibits glioblastoma growth in vivo. *Clin Cancer Res*. (2006); 12: 6144-52.

2) Jin, H., et al. MetMAb, the one-armed 5D5 anti-c-Met antibody, inhibits orthotopic pancreatic tumor growth and improves survival. *Cancer Res*. (2008); 68: 4360-8.

3) www.clinicaltrial.gov; Identifier: NCT01456325."A study of Onartuzumab (MetMab) in combination with Tarceva (Erlotinib) in patients with Met diagnostic-positive Non-Small Cell Lung cancer who have received chemotherapy for advanced or metastatic disease (MetLung)".

4) Prat, M., et al. Agonistic monoclonal antibodies against the Met receptor dissect the biological responses to HGF. *J Cell Sci*. (1998); 111: 237-47.

5) Petrelli, A., et al. Ab-induced ectodomain shedding mediates hepatocyte growth factor receptor down-regulation and hampers biological activity. *Proc Natl Acad Sci USA*. (2006); 103: 5090-5.

6) Foveau, B., et al. Down-regulation of the met receptor tyrosine kinase by presenilin-dependent regulated intramembrane proteolysis. *Mol Biol Cell*. (2009); 20: 2495-507.

7) Schelter, F, et al. A disintegrin and metalloproteinase-10 (ADAM-10) mediates DN30 antibody-induced shedding of the met surface receptor. *J Biol Chem*. (2010); 285: 26335-40.

8) Pacchiana G, et al. Monovalency unleashes the full therapeutic potential of the DN-30 anti-Met antibody. *J Biol Chem*. (2010); 285: 36149-57.

9) Reichert J M. Antibody-based therapeutics to watch in 2011. *MAbs*. (2011); 3: 76-99.

10) Michieli P, et al. An HGF-MSP chimera disassociates the trophic properties of scatter factors from their pro-invasive activity. *Nat Biotechnol* (2002); 20:488-495.

11) Giordano S, et al. p 145, A protein with associated tyrosine kinase activity in a human gastric carcinoma cell line. *Mol Cell Biol* 1988 8:3510-3517.

12) Longati P, et al. Tyrosines 1234-1235 are critical for activation of the tyrosine kinase encoded by the MET proto-oncogene (HGF receptor). *Oncogene* 1994 9:49-57.

13) Vigna E, et al. "Active" cancer immunotherapy by anti-Met antibody gene transfer. *Cancer Res* 2008 68:9176-9183.

The invention claimed is:

1. An isolated nucleic acid encoding a monovalent antibody fragment comprising
   a) a first polypeptide comprising one light chain variable domain and a first and second human light chain constant domain, wherein the light chain variable domain is fused to the first human light chain constant domain that is fused to the second human light chain constant domain in the N- to C-terminal direction, thus generating a VL-CL-CL chimeric light chain, and
   b) a second polypeptide comprising one heavy chain variable domain and a first and second human heavy chain CH1 constant domain, wherein the heavy chain variable domain is fused to the first human heavy chain CH1 constant domain that is fused to the second heavy chain CH1 constant domain in the N- to C-terminal direction, thus generating a VH-CH1-CH1 chimeric heavy chain,
   wherein the encoded monovalent antibody fragment specifically binds to hepatocyte growth factor receptor (HGFR).

2. The isolated nucleic acid encoding the monovalent antibody fragment according to claim 1, wherein both the first and second light chain constant domains are human kappa light chain constant domains.

3. The isolated nucleic acid encoding the monovalent antibody fragment according to claim 1, wherein both the first and second heavy chain CH1 constant domains are human gamma heavy chain CH1 constant domains.

4. The isolated nucleic acid encoding the monovalent antibody fragment according to claim 1, wherein the both the first and second heavy chain CH1 constant domains are from a human IgG1.

5. The isolated nucleic acid encoding the monovalent antibody fragment according to claim 1, wherein the light chain variable domain comprises the complementarity determining regions (CDRs) of SEQ ID NOS: 25, 27, and 29, and the heavy chain variable domain comprises the complementarity determining regions (CDRs) of SEQ ID NOS: 19, 21, and 23.

6. The isolated nucleic acid encoding the monovalent antibody fragment according to claim 1, wherein the light chain variable domain is selected between a non-human light chain variable domain or a human or humanized light chain variable domain, and wherein the heavy chain variable domain is selected between a non-human heavy chain variable domain or a human or humanized heavy chain variable domain.

7. The isolated nucleic acid encoding the monovalent antibody fragment of claim 1, wherein the first polypeptide comprises SEQ ID NO: 10, and the second polypeptide comprises SEQ ID NO: 2.

8. A composition comprising the nucleic acid encoding the antibody fragment according to claim 1, and a physiologically acceptable carrier.

9. An isolated nucleic acid encoding a monovalent antibody fragment comprising
   a) a first polypeptide comprising one light chain variable domain and one human light chain constant domain and one human heavy CH1 constant domain, wherein the light chain variable domain is fused to the human light chain constant domain, the human light chain constant domain is fused to the human heavy CH1 chain constant domain in the N- to C-terminal direction, thus generating a VL-CL-CH1 chimeric light chain, and
   b) a second polypeptide comprising one heavy chain variable domain and one human heavy CH1 constant domain and one human light chain constant domain, wherein the heavy chain variable domain is fused to the human heavy chain CH1 constant domain, and the human heavy chain CH1 constant domain is fused to the human light chain constant domain in the N- to C-terminal direction, thus generating a VH-CH1-CL chimeric heavy chain,
   wherein the encoded monovalent antibody fragment specifically binds to hepatocyte growth factor receptor (HGFR).

10. The isolated nucleic acid encoding the monovalent antibody fragment according to claim 9, wherein the light chain constant domain is a human kappa light chain constant domain.

11. The isolated nucleic acid encoding the monovalent antibody fragment according to claim 9, wherein the heavy chain CH1 constant domain is a human gamma heavy chain CH1 constant domain.

12. The isolated nucleic acid encoding the monovalent antibody fragment according to claim 9, wherein the heavy chain CH1 constant domain is from a human IgG1.

13. The isolated nucleic acid encoding the monovalent antibody fragment according to claim 9, wherein the light chain variable domain comprises the complementarity determining regions (CDRs) of SEQ ID NOS: 25, 27, and 29, and the heavy chain variable domain comprises the complementarity determining regions (CDRs) of SEQ ID NOS: 19, 21, and 23.

14. The isolated nucleic acid encoding the monovalent antibody fragment according to claim 9, wherein the light chain variable domain is selected between a non-human light chain variable domain or a human or humanized light chain variable domain, and wherein the heavy chain variable domain is selected between a non-human heavy chain variable domain or a human or humanized heavy chain variable domain.

15. The isolated nucleic acid encoding the monovalent antibody fragment of claim 9, wherein the first polypeptide comprises SEQ ID NO: 18, and the second polypeptide comprises SEQ ID NO: 16.

16. A composition comprising the isolated nucleic acid encoding the monovalent antibody fragment according to claim 9, and a physiologically acceptable carrier.

* * * * *